(12) United States Patent
Fukuda et al.

(10) Patent No.: US 7,459,561 B2
(45) Date of Patent: *Dec. 2, 2008

(54) N-SUBSTITUTED CARBAMOYLOXYALKYL-AZOLIUM DERIVATIVES

(75) Inventors: Hiroshi Fukuda, Tokyo (JP); Tadakatsu Hayase, Chigasaki (JP); Eisaku Mizuguchi, Kamakura (JP); Nobuo Shimma, Chigasaki (JP); Jun Ohwada, Kamakura (JP); Nobuhiro Oikawa, Kawasaki (JP); Masahiro Sakaitani, Chigasaki (JP); Masao Tsukazaki, Fujisawa (JP); Isao Umeda, Yokohama (JP)

(73) Assignee: Basilea Pharmaceutica AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/504,299

(22) Filed: Aug. 15, 2006

(65) Prior Publication Data

US 2007/0027322 A1 Feb. 1, 2007

Related U.S. Application Data

(62) Division of application No. 10/933,577, filed on Sep. 3, 2004, now Pat. No. 7,189,858, which is a division of application No. 09/702,944, filed on Oct. 31, 2000, now Pat. No. 6,812,238.

(30) Foreign Application Priority Data

Nov. 2, 1999 (EP) .................................. 99121694

(51) Int. Cl.
*C07D 401/14* (2006.01)
(52) U.S. Cl. ................................. 546/269.7
(58) Field of Classification Search ............... 546/269.7
See application file for complete search history.

(56) References Cited

U.S. PATENT DOCUMENTS

| 4,144,346 | A | 3/1979 | Heeres et al. |
| 6,265,584 | B1 | 7/2001 | Hudyma et al. |
| 6,300,353 | B1 | 10/2001 | Hayase et al. |
| 6,812,238 | B1 * | 11/2004 | Fukuda et al. .............. 514/342 |

FOREIGN PATENT DOCUMENTS

| DE | 28 04 096 | 8/1978 |
| EP | 0006711 | 1/1980 |
| EP | 0101360 | 2/1984 |
| EP | 0435081 | 7/1991 |
| EP | 0667346 | 8/1995 |
| JP | 11228548 | 8/1999 |
| WO | WO 98/43970 | 10/1998 |
| WO | WO 99/45008 | 9/1999 |

OTHER PUBLICATIONS

Patonay et al., Synthetic Communications, 26(22):4253-4265 (1996).
Davidson et al., J. Med. Chem., 37(26):4423-9 (1994/.
Med. Chem. Res., 7(2):123-136 (1997).
Godefroi et al., J. Med. Chem, 12:784-91 (1969).
Tasaka et al., Chem. Pharm. Bull., 45:321-6 (1997).
Kai et al., Chem. Pharm. Bull., 44:568-71 (1996).
Yamada, Antimicrob. Agents Chemother., 37:2412-7 (1993).
Turner, Curr. Pharm. Design, 2:209-224 (1996).
Tasaka, Chem. Pharm. Bull., 41:1035-1042 (1993).
Heeres et al., J. Med. Chem., 27:894-900 (1984).
Heeres et al., J. Med. Chem., 22:1003-5 (1979).
Drugs Future, 17:1145-6 (1992).

* cited by examiner

*Primary Examiner*—Patricia L Morris

(57) ABSTRACT

N-substituted carbamoyloxyalkyl-azolium derivatives which have antifungal activity and are useful for the treatment of fungal diseases.

21 Claims, No Drawings

N-SUBSTITUTED CARBAMOYLOXYALKYL-AZOLIUM DERIVATIVES

CROSS-REFERENCE TO RELATED APPLICATION

This Application is a Divisional of application Ser. No. 10/933,577, filed Sep. 3, 2004 now U.S. Pat. No. 7,189,858 which is a Divisional of application Ser. No. 09/702,944, filed Oct. 31, 2000 now U.S. Pat. No. 6,812,238.

BACKGROUND OF THE INVENTION

Although several azole compounds are currently used for systemic mycoses, none of them completely fulfills the necessary clinical requirements of efficacy against major systemic mycoses including disseminated aspergillosis, safety, and availability in oral or parenteral formulations. Demand for parenterally formulated azole compounds for the treatment of serious systemic mycoses is increasing. Most of the azole compounds on the market as well as under development are highly lipophilic molecules that make parenteral formulation difficult.

SUMMARY OF THE INVENTION

The present invention relates to novel water soluble azole compounds useful for the treatment of systemic mycoses and suitable for both oral and particularly parenteral administration, a process for their manufacture, antifungal compositions containing them and a method for treating mycoses.

More particularly, the present invention refers to compounds of formula (I), (I)

wherein
- Q is a 3H-imidazole or 1,2,4-triazole derivative with antifungal activity which is linked to the remainder of the compound of formula (I) by a nitrogen in the azole;
- $R^1$ is hydrogen or alkyl;
- $R^2$ is hydrogen, alkyl, alkylcarbonyloxyalkyl, alkoxycarbonyl, alkylcarbonyl, mono- or dialkylaminoalkylcarbonyloxyalkyl;
- $R^3$ is alkylaminoalkyl, alkylcarbonyl, alkylcarbonyloxyalkyl, alkylaminoalkylcarbonyloxyalkyl, hydrogen, acylalkylaminoalkyl, alkyl, hydroxyalkyl, aminoalkyl, alkylcarbonylaminoalkyl, alkylcarbonylalkylaminoalkyl, alkoxycarbonylalkylaminoalkyl, alkoxycarbonylaminoalkyl, optionally substituted phenyl, optionally substituted pyridin-2-yl or optionally substituted 5-or 6-membered cycloalkyl, acylaminoalkyl, alkylaminoalkylacyloxyalkyl or
- the group $(R^2, R^3)N$— may form an optionally substituted pyrrolidine, pyrrolidone or piperidine; and
- $X^-$ is a pharmaceutically acceptable anion, as well as pharmaceutically acceptable salts, hydrates or solvates of the compounds of formula (I).

DETAILED DESCRIPTION OF THE INVENTION

Preferably, $R^3$ is alkylaminoalkyl, alkylcarbonyl, alkylcarbonyloxyalkyl, alkylaminoalkylcarbonyloxyalkyl, optionally substituted phenyl, optionally substituted pyridin-2-yl or optionally substituted 5-or 6-membered cycloalkyl in compounds of formula I.

More preferably, $R^3$ is characterized by formula (II) as defined below, (II)

wherein
$R^1$, $R^2$, Q, and X are as defined in claim 1; group is phenyl or pyridin-2-yl;

$R^4$ and $R^5$ are independently selected from the group consisting of hydrogen, halogen, alkyl, alkoxy, alkylthio, alkylsulfinyl, alkylsulfonyl, carboxy, alkyloxycarbonyl, cyano, trifluoromethyl, trifluormethoxy, nitro, aminosulfonyl, alkylaminocarboyloxyalkyl, and sulfo when group is phenyl or pyridin-2-yl and are in addition alkylcarbonyloxyalkyl or aminoalkylcarbonyloxyalkyl when group is pyridin-2-yl and are in addition aminoalkylcarbonyl or alkylaminoalkyl when group is phenyl; and $R^6$ is hydroxy, alkoxycarbonylalkylamino, alkoxycarbonylamino, amino, alkylamino, alkylcarbonyloxy, alkoxycarbonylalkylaminoalkylcarbonyloxy, alkoxycarbonylamino-alkylcarbonyloxy, alkylaminoalkylcarbonyloxy, aminoalkylcarbonyloxy, alkylcarbonylamino, alkylcarbonylalkylamino, acyloxy, acylamino, acylalkylamino. Group

may be pyridin-2-yl substituted as described above, but is preferably substituted with alkylaminoalkylcarbonyloxyalkyl, alkylcarbonyloxyalkyl, or aminoalkylcarbonyloxyalkyl. Group

may be phenyl substituted as described above, but is preferably substituted with aminoalkylcarbonyl, nitro, alkylaminoalkyl, trifluoromethoxy, alkyl, halogen, alkoxy, cyano, or alkylaminoalkylcarbonyloxyalkyl or pyridin-2-yl substituted with alkylaminoalkylcarbonyloxyalkyl, alkylcarbonyloxyalkyl, or aminoalkylcarbonyloxyalkyl.

Preferably, the above compounds may be characterized by formula (III),

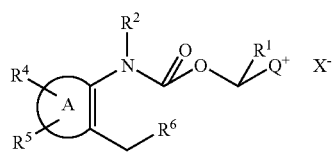

(III)

wherein $R^1$, $R^2$, Q, and X are as defined above; $R^4$ and $R^5$ are independently selected from the group consisting of hydrogen, halogen, alkyl, alkoxy, alkylthio, alkylsulfinyl, alkylsulfonyl, carboxy, alkoxycarbonyl, cyano, trifluoromethyl, trifluormethoxy, nitro, aminosulfonyl or sulfo; $R^6$ is hydroxy, alkoxycarbonylalkylamino, alkoxycarbonylamino, amino, alkylamino, alkylcarbonyloxy, alkoxycarbonylalkylaminoalkylcarbonyloxy, alkoxycarbonylamino-alkylcarbonyloxy, alkylaminoalkylcarbonyloxy, aminoalkylcarbonyloxy, alkylcarbonylamino, alkylcarbonylalkylamino, acyloxy, acylamino, acylalkylamino and the group

is phenyl or pyridin-2-yl.

In the above compounds of formula I (particularly formulae II, and III), it is preferred that $R^4$ and $R^5$ are independently selected from the group consisting of hydrogen, halogen, alkoxy, cyano, trifluoromethyl, trifluormethoxy and nitro, preferably hydrogen, halogen, and alkoxy, and especially hydrogen. It is also preferred that $R^6$ is alkylamino, alkylcarbonyloxy, alkylaminoalkylcarbonyloxy or aminoalkylcarbonyloxy, especially alkylaminoalkylcarbonyloxy.

In this specification the term "alkyl" refers to a branched or unbranched saturated hydrocarbon radical, consisting solely of carbon and hydrogen atoms, having 1 to 6, preferably 1 to 4 carbon atom(s), unless otherwise indicated, e.g. methyl, ethyl, n-propyl, iso-propyl, butyl, iso-butyl or tert-butyl n-pentyl or pentan-3-yl and the like.

The term "5- or 6-membered cycloalkyl" means a monovalent saturated carbocyclic radical, e.g. cyclopentyl and cylcohexyl. The term "optionally substituted 5- or 6-membered cycloalkyl" in the group $R^3$ means a 5- or 6-membered cycloalkyl as defined above optionally substituted with hydroxy, amino, alkylamino, acyloxy, acylamino or acylalkylamino wherein acyl means an easily hydrolyzable radical under physiological condition.

The terms "solvates" and "hydrates" refer to compounds, e.g. of formula (I), which additionally comprise solvent molecules or, in the case of hydrates, water molecules.

The "optionally substituted phenyl" means a phenyl optionally substituted with aminoalkylcarbonyl, nitro, alkylaminoalkyl, trifluoromethoxy, alkyl, halogen, alkoxy, cyano, or alkylaminoalkylcarbonyloxyalkyl. Other substituents are $R^4$, $R^5$ and —$CH_2$—$R^6$ as defined above. Thus compounds of formula I include phenyl substituted with aminoalkylcarbonyl, nitro, alkylaminoalkyl, trifluoromethoxy, alkyl, halogen, alkoxy, cyano, or alkylaminoalkylcarbonyloxyalkyl, and in addition with $R^4$, $R^5$ and —$CH_2$—$R^6$ as defined above.

The term "optionally substituted pyridin-2-yl" means a pyridin-2-yl optionally substituted with alkylaminoalkylcarbonyloxyalkyl, alkylcarbonyloxyalkyl, or aminoalkylcarbonyloxyalkyl. Other substituents are $R^4$, $R^5$ and —$CH_2$—$R^6$ as defined above. Thus compounds of formula I include pyridin-2-yl substituted with alkylaminoalkylcarbonyloxyalkyl, alkylcarbonyloxyalkyl, or aminoalkylcarbonyloxyalkyl and in addition with $R^4$, $R^5$ and —$CH_2$—$R^6$ as defined above.

Preferably, the terms "optionally substituted phenyl" and "optionally substituted pyridin-2-yl" refer to the group of formula (VI)

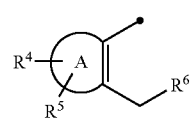

(VI)

wherein $R^4$, $R^5$ and $R^6$ are as defined above.

Preferably, $R^6$ is hydroxy, amino, alkylamino, acyloxy, acylamino or acyl, alkylamino, alkylaminoalkylcarbonyloxy, aminoalkylcarbonyloxy in which acyl means an easily hydrolyzable radical under physiological conditions.

The term "acyl" refers to an easily hydrolyzable radical under physiological which preferably means an acyl residue of an amino acid or a group represented by the formula, $R^7CO—$ or $(R^8O)_2PO—$, wherein $R^7$ is hydrogen, alkoxy, alkyl which may be optionally substituted with carboxy, amino, alkylamino, dialkylamino, or aryl, preferably phenyl; and $R^8$ is hydrogen or alkyl.). More preferably, "acyl" is formyl, acetyl, propionyl, isobutyryl, pivaloyl, succinoyl, benzoyl, nicotinoyl, phosphoryl, dimethylphosphoryl, aminoacetyl, 3-aminopropionyl, 4-aminobutyryl, (2-aminoacetylamino)-acetyl, (S)-2,5-diaminopentoyl, (S)-2-aminopropionyl, (S)-pyrrolidine-2-carbonyl, (methylamino)acetyl, (propylamino)acetyl, (S)-2-(methylamino)propionyl, 3-(methylamino)propionyl, (S)-2-amino-3-methylbutanoyl, (isopropylamino)acetyl, (2S)-2-(ethylamino)propionyl, (ethylamino)acetyl and the like.

The term "alkoxy" refers to preferably straight or branched alkyl-O— chain having 1 to 5 carbon atom(s) such as methoxy, ethoxy, n-propoxy, iso-propoxy, n-butoxy, iso-butoxy.

The term "halogen" denotes fluorine, chlorine or bromine.

The term "alkylthio" refers to preferably straight or branched alkyl-S— chain having 1 to 4 carbon atom(s) such as methylthio, ethylthio, n-propylthio.

X⁻ is an anion from a pharmaceutically acceptable inorganic acid, e.g. a mineral acid; such as chloride, bromide or sulfate; or from an organic acid, e.g. an aliphatic, aromatic or arylaliphatic carboxylic or sulfonic acid such as acetoxy, trifluoroacetoxy, mesyloxy anion and the like.

The term "leaving group" refers to chloro, bromo, iodo, tosyloxy, mesyloxy and the like.

The term "carbonyl" refers to the group —C(O)—.
The term "oxy" refers to the group —O—.
The term "amino" refers to —NH$_2$.
The term "sulfinyl" refers to the group —SO—.
The term "sulfonyl" refers to the group —SO$_2$—.
The term "sulfo" refers to the group HO—SO$_2$—.

In a more preferred embodiment, the above compounds may be characterized by formula (III),

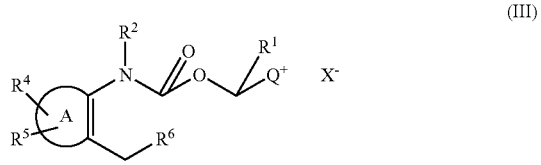

(III)

wherein R$^1$, R$^2$, Q, and X are as defined above and R$^4$ and R$^5$ are independently selected from the group consisting of hydrogen, halogen, alkyl, alkoxy, alkylthio, alkylsulfinyl, alkylsulfonyl, carboxy, alkoxycarbonyl, cyano, trifluoromethyl, trifluormethoxy, nitro, aminosulfonyl or sulfo; R$^6$ is hydroxy, alkoxycarbonylalkylamino, alkoxycarbonylamino, amino, alkylamino, alkylcarbonyloxy, alkoxycarbonylalkylamino-alkylcarbonyloxy, alkoxycarbonylamino-alkylcarbonyloxy, alkylaminoalkylcarbonyloxy, aminoalkylcarbonyloxy, alkylcarbonylamino, alkylcarbonylalkylamino, acyloxy, acylamino, acylalkylamino; the group

is phenyl or pyridin-2-yl.

In compounds of formula I, such as compound of formulae II and III, it is preferred that group Q is one of the following:
a) 1-[2-(2,4-Dichlorophenyl)-2-[(2,4-dichlorophenyl)methoxy]ethyl]-1H-imidazole (Miconazole),
b) cis-1-Acetyl-4-[4-[[2-(2,4-dichlorophenyl)-2-(1H-imidazol-1-ylmethyl)-1,3-dioxolan-4-yl]methoxy]phenyl]piperazine (Ketoconazole),
c) 4-[4-[4-[4-[[2-(2,4-Dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-[1,2,4]triazol-3-one (Itraconazole),
d) 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone,
e) (+)-2-(2,4-Difluorophenyl)-3-methyl-1-(1H-1,2,4-triazol-1-yl)-3-(6-(1H-1,2,4-triazol-1-yl)pyridazin-3-ylthio)butan-2-ol,
f) (2R)-2-(2,4-diflourophenyl)-1-[3-[(E)-4-(2,2,3,3-tetrafluoropropoxy)-styryl]-(1,2,4-triazol-1-yl)-3-(1,2,4-triazol-1-yl)]propan-2-ol,
g) dl-Threo-2-(2,4-difluorophenyl)-3-methyl-sulfonyl-1-(1H-1,2,4-triazol-1-yl)-butan-2-ol,
h) (−)-4-[4-[4-[4-[[5-(2,4-Difluorophenyl)-5-(1H-1,2,4-triazol-1-ylmethyl)tetrahydro-furan-3-yl]methoxy]phenyl]piperazinyl]phenyl]-2[(1S,2S)-1-ethyl-2-hydroxypropyl]-3H-1,2,4-triazol-3-one,
i) (2R,3R)-3-[4-(4-cyanophenyl)thiazol-2-yl)]-2-(2,4-difluorophenyl)-1-(1H-1,2,4-triazol-1-yl)-butan-2-ol,
j) 3-Methyl-3-methylthio-1-(1,2,4-triazol-1-yl)-2-(trifluoromethylphenyl)-butan-2-ol,
k) (2R,3R)-3-[4-(4-cyanophenyl)thiazol-2-yl)]-1-(1H-1,2,4-triazol-1-yl)-2-(2,4,5-trifluorophenyl)-butan-2-ol,
l) (2R,3R)-3-[4-(4-cyanophenyl)thiazol-2-yl)]-2-(2,5-difluorophenyl)-1-(1H-1,2,4-triazol-1-yl)-butan-2-ol, and
m) (2R,3R)-3-[4-(4-cyanophenyl)thiazol-2-yl)]-2-(3-fluorophenyl)-1-(1H-1,2,4-triazole-1-yl)-butan-2-ol.

The most preferred embodiment of group Q is a group of the following structure:

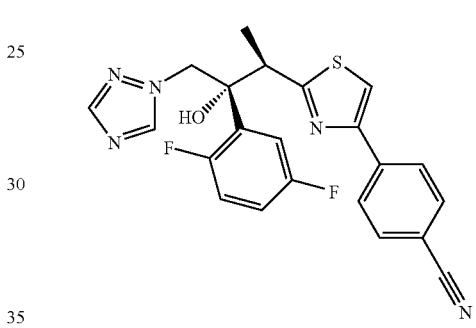

This is especially preferred for compounds of formulae II and III, and even more preferably in the following embodiments:

In a further preferred embodiment of the invention are compounds wherein R$^1$ is hydrogen or alkyl, preferably methyl. R$^2$ is hydrogen, alkyl, alkylcarbonyloxyalkyl, alkoxycarbonyl, alkylcarbonyl, mono- or dialkylaminoalkylcarbonyloxyalkyl, preferably hydrogen or alkyl, more preferably alkyl, e.g. methyl. R$^3$ in the above compounds is alkylaminoalkyl, alkylcarbonyl, alkylcarbonyloxyalkyl, alkylaminoalkylcarbonyloxyalkyl, hydrogen, alkyl, hydroxyalkyl, aminoalkyl, alkylcarbonylaminoalkyl, alkylcarbonylalkylaminoalkyl, alkoxycarbonylalkylaminoalkyl, alkoxycarbonylaminoalkyl, optionally substituted phenyl, optionally substituted pyridin-2-yl or optionally substituted 5-or 6-membered cycloalkyl, acylaminoalkyl, alkylaminoalkylacyloxyalkyl or, more preferably alkylaminoalkyl, alkylcarbonyl, alkylcarbonyloxyalkyl, alkylaminoalkylcarbonyloxyalkyl, optionally substituted phenyl, optionally substituted pyridin-2-yl or optionally substituted 5-or 6-membered cycloalkyl and most preferably substituted pyridin-2-yl. In a further preferred embodiment the invention comprises compounds wherein the group (R$^2$, R$^3$)N— forms an optionally substituted pyrrolidine, pyrrolidone or piperidine, preferably an optionally substituted pyrrolidine. Preferred optional substituents for such a pyrrolidine, pyrrolidone or piperidine are amino, aminomethyl or (methylamino)acetoxymethyl. All or any combination of the above embodiments are preferred for compounds of formulae II and III.

Further the invention includes the above-defined compounds wherein Y is methine (═CH—) or nitrogen, preferably nitrogen, i.e. where Q is 1H-imidazole or 1,2,4-triazole, preferably 1,2,4-triazole. In the preferred compounds, X is halogen, preferably chloro. In a preferred embodiment of the above invention $R^4$ and $R^5$ are independently selected from the group consisting of hydrogen, halogen, alkyl, alkoxy, alkylthio, alkylsulfinyl, alkylsulfonyl, carboxy, alkoxycarbonyl, cyano, trifluormethoxy, nitro, aminosulfonyl or sulfo, preferably from hydrogen, halogen, alkoxy, cyano, trifluoromethyl, trifluormethoxy and nitro. In a preferred embodiment, $R^4$ and $R^5$ independently are selected from hydrogen, halogen and alkoxy, most preferably $R^4$ and $R^5$ both are hydrogen. All or any combination of the above embodiments are preferred for compounds of formulae II and III.

In another preferred embodiment the invention comprises compounds wherein $R^6$ is hydroxy, alkoxycarbonylalkylamino, alkoxycarbonylamino, amino, alkylamino, alkylcarbonyloxy, alkoxycarbonylalkylamino-alkylcarbonyloxy, alkoxycarbonylamino-alkylcarbonyloxy, alkylaminoalkylcarbonyloxy, aminoalkylcarbonyloxy, alkylcarbonylamino, alkylcarbonylalkylamino, acyloxy, acylamino, acylalkylamino, acylalkylamino, preferably $R^6$ is alkylamino, alkylcarbonyloxy, alkylaminoalkylcarbonyloxy, or aminoalkylcarbonyloxy, more preferably $R^6$ is acyloxy in which acyl is the acyl residue of an amino acid such as sarcosyl, alanyl, seryl, cysteinyl and the like, e.g. alkylaminoalkylcarbonyloxy. All or any combination of the above embodiments are preferred for compounds of formulae II and III.

In addition the present invention comprises compounds wherein the group

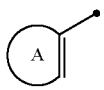

is optionally substituted phenyl or pyridin-2-yl, preferably pyridin-2-yl.

In the most preferred embodiment the invention refers to the above compounds of formula (I) wherein Q is

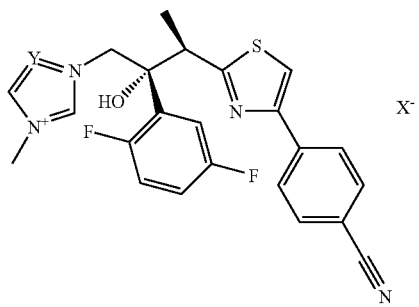

Y is nitrogen or =CH—, $R^1$ is alkyl, $R^2$ is alkyl, $R^3$ is optionally substituted pyridin-2-yl, $X^-$ is halogen, $R^4$ and $R^5$ are hydrogen, $R^6$ is alkylaminoalkylcarbonyloxy, and pharmaceutically acceptable salts, hydrates or solvates thereof.

Especially the invention refers to the following compounds selected from the group consisting of:

a) 1-[[N-methyl-N-2-(methylamino)acetoxymethyl-3-chloro-phenyl]carbamoyloxy]ethyl-3-[2-(2,4-dichlorobenzyloxy)-2-(2,4-dichlorophenyl)ethyl]-3H-imidazol-1-ium chloride hydrochloric acid, b) 1-[[N-methyl-N-2-(methylamino)acetoxymethyl-5-chloro-phenyl]carbamoyloxy]ethyl-3-[2-(2,4-dichlorobenzyloxy)-2-(2,4-dichlorophenyl)ethyl]-3H-imidazol-1-ium chloride hydrochloric acid, c) 1-[[N-methyl-N-3-[(methylamino)acetoxymethyl]pyridin-2-yl]carbamoyloxy]ethyl-3-[2-(2,4-dichlorobenzyloxy)-2-(2,4-dichlorophenyl)ethyl]-3H-imidazol-1-ium chloride dihydrochloric acid, d) 1-[[N-methyl-N-2-(methylamino)acetoxymethyl-3-chloro-phenyl]carbamoyloxy]ethyl-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium chloride hydrochloric acid, e) 1-[[N-methyl-N-2-(methylamino)acetoxymethyl-5-chloro-phenyl]carbamoyloxy]ethyl-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium chloride hydrochloric acid, f) 1-[[N-methyl-N-3-[(methylamino)acetoxymethyl]pyridin-2-yl]carbamoyloxy]ethyl-3-[(2R,4S)-4-[4-(4-acetylpiperazin-1-yl)phenoxymethyl]-2-(2,4-dichlorophenyl)-[1,3]dioxan-2-ylmethyl]-3H-imidazol-1-ium chloride dihydrochloric acid, g) 1-[[N-methyl-N-2-(methylamino)acetoxymethyl-3-chloro-phenyl]carbamoyloxy]ethyl-1-[4-[4-[4-(1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium chloride hydrochloric acid, h) 1-[[N-methyl-N-2-(methylamino)acetoxymethyl-5-chloro-phenyl]carbamoyloxy]ethyl-1-[4-[4-[4-(1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium chloride hydrochloric acid, i) 1-[[N-methyl-N-3-[(methylamino)acetoxymethyl]pyridin-2-yl]carbamoyloxy]ethyl-1-[4-[4-[4-(1-(2-butyl-5-oxo-1,5-dihydro-[1,2,4]triazol-4-yl)phenyl]piperazin-1-yl]phenoxymethyl]-2-(2,4-dichlorophenyl)-[1,3]dioxolan-2-ylmethyl]-1H-[1,2,4]triazol-4-ium chloride dihydrochloric acid, j) 1-[[N-methyl-N-2-(methylamino)acetoxymethyl-3-chloro-phenyl]carbamoyloxy]ethyl-1-[(2R,3R)-2-(2,4-difluorophenyl)-2-hydroxy-3-{5-oxo-4-[4-(2,2,3,3-tetrafluoropropoxy)phenyl]-4,5-dihydro-[1,2,4]triazol-1-yl}butyl]-1H-[1,2,4]triazol-4-ium chloride hydrochloric acid, k) 1-[[N-methyl-N-2-(methylamino)acetoxymethyl-5-chloro-phenyl]carbamoyloxy]ethyl-1-[(2R,3R)-2-(2,4-difluorophenyl)-2-hydroxy-3-{5-oxo-4-[4-(2,2,3,3-tetrafluoropropoxy)phenyl]-4,5-dihydro-[1,2,4]triazol-1-yl}butyl]-1H-[1,2,4]triazol-4-ium chloride hydrochloric acid, l) 1-[[N-methyl-N-3-[(methylamino)acetoxymethyl]pyridin-2-yl]carbamoyloxy]ethyl-1-[(2R,3R)-2-(2,4-difluorophenyl)-2-hydroxy-3-{5-oxo-4-[4-(2,2,3,3-tetrafluoropropoxy)phenyl]-4,5-dihydro-[1,2,4]triazol-1-yl}butyl]-1H-[1,2,4]triazol-4-ium chloride dihydrochloric acid, m) 1-[[N-methyl-N-2-(methylamino)acetoxymethyl-3-chloro-phenyl]carbamoyloxy]ethyl-1-[(2R)-2-(2,4-difluorophenyl)-2-hydroxy-3-methyl-3-(6-[1,2,4]triazol-1-yl-pyridazin-3-ylsulfanyl)butyl]-1H-[1,2,4]triazol-4-ium chloride hydrochloric acid, n) 1-[[N-methyl-N-2-(methylamino)acetoxymethyl-5-chloro-phenyl]carbamoyloxy]ethyl-1-[(2R)-2-(2,4-difluorophenyl)-2-hydroxy-3-methyl-3-(6-[1,2,4]triazol-1-yl-pyridazin-3-ylsulfanyl)butyl]-1H-[1,2,4]triazol-4-ium chloride hydrochloric acid, o) 1-[[N-methyl-N-3-[(methylamino)acetoxymethyl]pyridin-2-yl]carbamoyloxy]ethyl-1-[(2R)-2-(2,4-difluorophenyl)-2-hydroxy-3-methyl-3-(6-[1,2,4]triazol-1-yl-pyridazin-3-ylsulfanyl)butyl]-1H-[1,2,4]triazol-4-ium chloride dihydrochloric acid, p) 1-[[N-methyl-N-2-(methylamino)acetoxymethyl-3-chloro-phenyl]carbamoyloxy]ethyl-1-[(2R)-2-(2,4-difluorophenyl)-2-hydroxy-3-(3-{(Z)-2-[4-(2,2,3,3-tetrafluoropropoxy)phenyl]vinyl}-[1,2,4]triazol-1-yl)propyl]-1H-[1,2,4]triazol-4-ium chloride hydrochloric acid, q) 1-[[N-methyl-N-2-(methylamino)acetoxymethyl-5-chloro-phenyl]carbamoyloxy]ethyl-1-[(2R)-2-(2,4-difluorophenyl)-2-hydroxy-3-(3-{(Z)-2-[4-(2,2,3,3-tetrafluoropropoxy)phenyl]vinyl}-[1,2,4]triazol-1-yl)propyl]-1H-[1,2,4]triazol-4-ium chloride hydrochloric acid, r) 1-[[N-methyl-N-3-[(methylamino)acetoxymethyl]pyridin-2-yl]carbamoyloxy]ethyl-1-[(2R)-2-(2,4-difluorophenyl)-2-hydroxy-3-(3-{(Z)-2-[4-(2,2,3,3-tetrafluoropropoxy)phenyl]vinyl}-[1,2,4]triazol-1-yl)propyl]-1H-[1,2,4]triazol-4-ium chloride dihydrochloric acid, s) 1-[[N-methyl-N-2-(methylamino)acetoxymethyl-3-chloro-phenyl]carbamoyloxy]ethyl-1-[(2R,3R)-2-(2,4-difluorophenyl)-2-hydroxy-3-methanesulfonylbutyl]-1H-[1,2,4]triazol-4-ium chloride hydrochloric acid, t) 1-[[N-methyl-N-2-(methylamino)acetoxymethyl-5-chloro-phenyl]carbamoyloxy]ethyl-1-[(2R,3R)-2-(2,4-difluorophenyl)-2-hydroxy-3-methanesulfonylbutyl]-1H-[1,2,4]triazol-4-ium chloride hydrochloric acid, u) 1-[[N-methyl-N-3-[(methylamino)acetoxymethyl]pyridin-2-yl]carbamoyloxy]ethyl-1-[(2R,3R)-2-(2,4-difluorophenyl)-2-hydroxy-3-methanesulfonylbutyl]-1H-[1,2,4]triazol-4-ium chloride dihydrochloric acid, v) 1-[[N-methyl-N-2-(methylamino)acetoxymethyl-3-chloro-phenyl]carbamoyloxy]ethyl-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-yl methyl]-1H-[1,2,4]triazol-4-ium chloride hydrochloric acid, w) 1-[[N-methyl-N-2-(methylamino)acetoxymethyl-5-chloro-phenyl]carbamoyloxy]ethyl-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-yl methyl]-1H-[1,2,4]triazol-4-ium chloride hydrochloric acid, x) 1-[[N-methyl-N-3-[(methylamino)acetoxymethyl]pyridin-2-yl]carbamoyloxy]ethyl-1-[(2R-cis)-2-(2,4-difluorophenyl)-4-[4-[4-[4-[1-[(1S,2S)-1-ethyl-2-hydroxypropyl]-5-oxo-1,5-dihydro-[1,2,4]triazol-4-yl]phenyl]piperazin-1-yl]phenoxymethyl]tetrahydrofuran-2-yl methyl]-1H-[1,2,4]triazol-4-ium chloride dihydrochloric acid, y) 1-[[N-methyl-N-2-(methylamino)acetoxymethyl-3-chloro-phenyl]carbamoyloxy]ethyl-1-[(2R,3R)-2-(2,4-difluorophenyl)-2-hydroxy-3-[4-(4-cyanophenyl)thiazol-2-yl]butyl]-1H-[1,2,4]triazol-4-ium chloride hydrochloride, z) 1-[[N-methyl-N-2-(methylamino)acetoxymethyl-5-chloro-phenyl]carbamoyloxy]ethyl-1-[(2R,3R)-2-(2,4-difluorophenyl)-2-hydroxy-3-[4-(4-cyanophenyl)thiazol-2-yl]butyl]-1H-[1,2,4]triazol-4-ium chloride hydrochloride, aa) 1-[[N-methyl-N-3-[(methylamino)acetoxymethyl]pyridin-2-yl]carbamoyloxy]ethyl-1-[(2R,3R)-2-(2,4-difluorophenyl)-2-hydroxy-3-[4-(4-cyanophenyl)thiazol-2-yl]butyl]-1H-[1,2,4]triazol-4-ium chloride dihydrochloride, bb) 1-[[N-methyl-N-2-(methylamino)acetoxymethyl-3-chloro-phenyl]carbamoyloxy]ethyl-1-[2-hydroxy-3-methyl-3-methylsulfanyl-2-(4-trifluoromethylphenyl)butyl]-1H-[1,2,4]triazol-4-ium chloride hydrochloric acid, cc) 1-[[N-methyl-N-2-(methylamino)acetoxymethyl-5-chloro-phenyl]carbamoyloxy]ethyl-1-[2-hydroxy-3-methyl-3-methylsulfanyl-2-(4-trifluoromethylphenyl)butyl]-1H-[1,2,4]triazol-4-ium chloride hydrochloric acid, dd) 1-[[N-methyl-N-3-[(methylamino)acetoxymethyl]pyridin-2-yl]carbamoyloxy]ethyl-1-[2-hydroxy-3-methyl-3-methylsulfanyl-2-(4-trifluoromethylphenyl)butyl]-1H-[1,2,4]triazol-4-ium chloride dihydrochloric acid, ee) 1-[[N-methyl-N-2-(methylamino)acetoxymethyl-3-chloro-phenyl]carbamoyloxy]ethyl-1-[(2R,3R)-2-(2,4,5-trifluorophenyl)-2-hydroxy-3-[4-(4-cyanophenyl)thiazol-2-yl]butyl]-1H-[1,2,4]triazol-4-ium chloride hydrochloride, ff) 1-[[N-methyl-N-2-(methylamino)acetoxymethyl-5-chloro-phenyl]carbamoyloxy]ethyl-1-[(2R,3R)-2-(2,4,5-trifluorophenyl)-2-hydroxy-3-[4-(4-cyanophenyl)thiazol-2-yl]butyl]-1H-[1,2,4]triazol-4-ium chloride hydrochloride, gg) 1-[[N-methyl-N-3-[(methylamino)acetoxymethyl]pyridin-2-yl]carbamoyloxy]ethyl-1-[(2R,3R)-2-(2,4,5-trifluorophenyl)-2-hydroxy-3-[4-(4-cyanophenyl)thiazol-2-yl]butyl]-1H-[1,2,4]triazol-4-ium chloride dihydrochloride, hh) 1-[[N-methyl-N-2-(methylamino)acetoxymethyl-3-chloro-phenyl]carbamoyloxy]ethyl-1-[(2R,3R)-2-(3-fluorophenyl)-2-hydroxy-3-[4-(4-cyanophenyl)thiazol-2-yl]butyl]-1H-[1,2,4]triazol-4-ium chloride hydrochloride, ii) 1-[[N-methyl-N-2-(methylamino)acetoxymethyl-5-chloro-phenyl]carbamoyloxy]ethyl-1-[(2R,3R)-2-(3-fluorophenyl)-2-hydroxy-3-[4-(4-cyanophenyl)thiazol-2-yl]butyl]-1H-[1,2,4]triazol-4-ium chloride hydrochloride and jj) 1-[[N-methyl-N-3-[(methylamino)acetoxymethyl]pyridin-2-yl]carbamoyloxy]ethyl-1-[(2R,3R)-2-(3-fluorophenyl)-2-hydroxy-3-[4-(4-cyanophenyl)thiazol-2-yl]butyl]-1H-[1,2,4]triazol-4-ium chloride dihydrochloride and pharmaceutically acceptable salts, hydrates or solvates thereof.

In addition, the invention refers to the compounds selected from the group consisting of a) [[N-methyl-N-2-(acetoxymethyl)phenyl]carbamoyloxy] methyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride, b) 1-[[N-methyl-N-2-(isopropylaminomethyl)phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, c) 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride dihydrochloride, d) 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, e) 1-[[N-ethyl-N-2-(ethylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, f) [[N-methyl-N-phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride, g) 1-[[N-methyl-N-3-(acetoxymethyl)pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, h) 1-[(N-acetyl-N-methyl) carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide, i) [[2(S)-(acetoxymethyl)pyrrolidin-1-yl]carbonyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide, j) [[N-methyl-N-2-(acetoxy)ethyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide, k) [[N-methyl-N-3-(acetoxy)propyl)]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide, l) [[N-2-(methyl)phenyl-N-2-(acetoxy)ethyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide, m) 1-[[N-2-[(isopropylamino)methyl]phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, n) 1-[[N-2-[(pentan-3-ylamino)methyl]phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, o) 1-[[N-methyl-N-2-[(methylamino)methyl]phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, p) [[N-methyl-N-2-[(methylamino)acetoxymethyl]phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, q) 1-[[N-methyl-N-2-[(methylamino)acetoxymethyl]phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, r) 1-[[N-methyl-N-2-(methylamino)acetoxymethyl-4,5-difluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, s) 1-[[N-methyl-N-2-(methylamino)acetoxymethyl-4-fluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, t) [[N-methyl-N-2-(methylamino)acetoxymethyl-4,5-dimethoxy-phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, u) 1-[[N-methyl-N-2-(methylamino)acetoxymethyl-5-fluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, v) 1-[[N-methyl-N-2-(methylamino)acetoxymethyl-6-methyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, w) 1-[[N-methyl-N-2-(methylamino)acetoxymethyl-4-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, x) 1-[[N-(methylamino)acetoxyethyl-N-2,4-difluorophenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, y) 1-[[N-methyl-N-2-(methylamino)acetoxymethyl-5-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, z) 1-[[N-methyl-N-2-(methylamino)acetoxymethyl-5-nitrophenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, aa) [[5(S)-(methylamino)acethoxymethyl-2-pyrrolidon-1-yl]carbonyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide, hydrochloride, bb) 1-[[N-methyl-N-2-(methylamino)acetoxymethyl-3-fluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, cc) 1-[[N-methyl-N-2-(methylamino)acetoxymethyl-5-cyano-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, dd) 1-[[N-methyl-N-2-(methylamino)acetoxymethyl-3-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, ee) 1-[[N-methyl-N-2-(methylamino)acetoxymethyl-4-cyano-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, ff) 1-[[N-methyl-N-2-(methylamino)acetoxymethyl-5-trifluoromethyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, gg) 1-[[N-methyl-N-2-(amino)acetoxymethyl-3-chloro-phenyl]carbamoyloxy]ethyl-1-[(2R,3R) -2-(2,5-difluorophenyl)-2-hydroxy-3-[4-(4-cyanophenyl)thiazol-2-yl]butyl]-1H-[1,2,4]triazol-4-ium chloride hydrochloride, hh) 1-[[N-ethyl-N-2-(methylamino)acetoxymethyl-3-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, ii) 1-[[N-methyl-N-3-[(amino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, jj) 1-[[N-methyl-N-2-(methylamino)acetoxymethyl-3-methyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, kk) 1-[[N-ethoxycarbonyl-N-2-(methylamino)acetoxymethyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, ll) 1-[[N-pivaloyl-N-2-(methylamino)acetoxymethyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, mm) 1-[[N-(methylamino)acetoxyethyl-N-pivaloyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, nn) 1-[[N-(methylamino)acetoxyethyl-N-ethoxycarbonyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, oo) 1-[[N-methyl-N-2(methylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, pp) 1-[[N-methyl-N-3-(methylamino)propyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, qq) 1-[[3(S)-amino-pyrrolidin-1-yl]carbonyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, rr) 1-[[2(S)-aminomethyl-pyrrolidin-1-yl]carbonyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride, ss) 1-[[N-methyl-N-2-(methylamino)-1,2-trans-cyclohexan-1-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride, and pharmaceutically acceptable salts, hydrates or solvates thereof.

The most preferred compound is 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride and pharmaceutically acceptable salts, hydrates or solvates thereof.

A further embodiment of the present invention is directed to intermediates useful for the preparation of the above-defined compounds. Preferred intermediates are compounds of formula (IV)

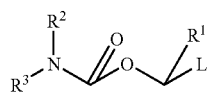
(IV)

wherein $R^1$, $R^2$, $R^3$ are as defined above in formula (I) and L is a leaving group.

In a more preferred embodiment the present invention comprises intermediates of formula (V)

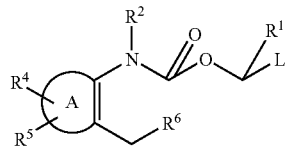
(V)

wherein $R^1$, $R^2$, $R^4$, $R^5$, $R^6$ and the group

are as defined above in formula (I) and L is a leaving group. Preferred compounds of formulae (IV) and (V) are compounds selected from the group consisting of a) [N-methyl-N-2-(acetoxymethyl)phenyl]carbamic acid chloromethyl ester,
b) [N-methyl-N-2-((tert-butoxycarbonylisopropylamino)methyl)phenyl]carbamic acid 1-chloro-ethyl ester,
c) [N-methyl-N-3-((tert-butoxycarbonylmethylamino)acetoxymethyl)pyridin-2-yl]carbamic acid 1-chloro-ethyl ester,
d) [N-ethyl-N-(tert-butoxycarbonyl ethylamino)ethyl]carbamic acid 1-chloro-ethyl ester,
e) [N-methyl-N-phenyl]carbamic acid chloromethyl ester,
f) [N-methyl-N-3-(acetoxymethyl)pyridin-2-yl]carbamic acid 1-chloro-ethyl ester,
g) [N-acety-N-methyl]carbamic acid 1-chloro-ethyl ester,
h) 2(S)-[acetoxymethyl]-1-[chloromethyloxycarbonyl]pyrrolidine,
i) [N-methyl-N-acetoxyethyl]carbamic acid chloromethyl ester,
j) [N-methyl-N-3-(acetoxy)propyl]carbamic acid chloromethyl ester,
k) [N-2-(methyl)phenyl-N-acetoxyethyl]carbamic acid chloromethyl ester,
l) [N-2-[(tert-butoxycarbonylisopropylamino)methyl]phenyl]carbamic acid 1-chloro-ethyl ester,
m) [N-2-[(tert-butoxycarbonyl-pentan-3-ylamino)methyl]phenyl]carbamic acid 1-chloro-ethyl ester,
n) [N-methyl-N-2-[(tert-butoxycarbonylmethylamino)methyl]phenyl]carbamic acid 1-chloro-ethyl ester,
o) [N-methyl-N-2-[(tert-butoxycarbonyl methylamino)acetoxymethyl]phenyl]carbamic acid chloromethyl ester,
p) [N-methyl-N-2-[(tert-butoxycarbonyl methylamino)acetoxymethyl]phenyl]carbamic acid 1-chloro-ethyl ester,
q) [N-methyl-N-2-[(tert-butoxycarbonylmethylamino)acetoxymethyl]-4,5-difluoro-phenyl]carbamic acid 1-chloro-ethyl ester,
r) [N-methyl-N-2-[(tert-butoxycarbonylmethylamino)acetoxymethyl]-4-fluoro-phenyl]carbamic acid 1-chloro-ethyl ester,
s) [N-methyl-N-2-[(tert-butoxycarbonylmethylamino)acetoxymethyl]-4,5-dimethoxy-phenyl]carbamic acid chloromethyl ester,
t) [N-methyl-N-2-[(tert-butoxycarbonylmethylamino)acetoxymethyl]-5-fluoro-phenyl]carbamic acid 1-chloro-ethyl ester,
u) [N-methyl-N-2-[(tert-butoxycarbonylmethylamino)acetoxymethyl]-6-methyl-phenyl]carbamic acid 1-chloro-ethyl ester,
v) [N-methyl-N-2-[(tert-butoxycarbonylmethylamino)acetoxymethyl]-4-chloro-phenyl]carbamic acid 1-chloro-ethyl ester,
w) [N-(tert-butoxycarbonylmethylamino)acetoxyethyl-N-2,4-difluorophenyl]carbamic acid 1-chloro-ethyl ester,
x) [N-methyl-N-2-[(tert-butoxycarbonylmethylamino)acetoxymethyl]-5-chloro-phenyl]carbamic acid 1-chloro-ethyl ester,
y) [N-methyl-N-2-[(tert-butoxycarbonylmethylamino)acetoxymethyl]-5-nitro-phenyl]carbamic acid 1-chloro-ethyl ester,
z) 5(S)-[(tert-butoxycarbonyl)methylaminoacethoxymethyl]-1-[chloromethyloxycarbonyl]-2-pyrrolidone,
aa) [N-methyl-N-2-[(tert-butoxycarbonylmethylamino)acetoxymethyl]-3-fluoro-phenyl]carbamic acid 1-chloro-ethyl ester, bb) [N-methyl-N-2-[(tert-butoxycarbonylmethylamino)acetoxymethyl]-5-cyano-phenyl]carbamic acid 1-chloroethyl ester,
cc) [N-methyl-N-2-[(tert-butoxycarbonylmethylamino)acetoxymethyl]-3-chloro-phenyl]carbamic acid 1-chloroethyl ester,
dd) [N-methyl-N-2-[(tert-butoxycarbonylmethylamino)acetoxymethyl]-4-cyano-phenyl]carbamic acid 1-chloroethyl ester,
ee) [N-methyl-N-2-[(tert-butoxycarbonylmethylamino)acetoxymethyl]-5-trifluoromethyl-phenyl]carbamic acid 1-chloro-ethyl ester,
ff) [N-methyl-N-2-[(tert-butoxycarbonylamino)acetoxymethyl]-3-chloro-phenyl]carbamic acid 1-chloro-ethyl ester,
gg) [N-ethyl-N-2-[(tert-butoxycarbonylmethylamino)acetoxymethyl]-3-chloro-phenyl]carbamic acid 1-chloroethyl ester,
hh) [N-methyl-N-3-[(tert-butoxycarbonylamino)acetoxymethyl]pyridin-2-yl]carbamic acid 1-chloro-ethyl ester,
ii) [N-methyl-N-2-[(tert-butoxycarbonylmethylamino)acetoxymethyl]-3-methyl-pheny]carbamic acid 1-chloroethyl ester,
jj) [N-ethoxycarbonyl-N-2-((tert-butoxycarbonylmethylamino)acetoxymethyl)pheny]carbamic acid 1-chloroethyl ester,
kk) [N-pivaloyl-N-2-((tert-butoxycarbonylmethylamino)acetoxymethyl)phenyl]carbamic acid 1-chloro-ethyl ester,
ll) [N-pivaloyl-N-2-(tert-butoxycarbonylmethylaminoacetoxy)ethyl]carbamic acid 1-chloro-ethyl ester,
mm) [N-ethoxycarbonyl-N-2-(tert-butoxycarbonylmethylaminoacetoxy)ethyl]carbamic acid 1-chloro-ethyl ester,
nn) [N-methyl-N-2-(tert-butoxycarbonyl methylamino)ethyl]carbamic acid 1-chloro-ethyl ester,
oo) [N-methyl-N-3-(tert-butoxycarbonyl methylamino)propyl]carbamic acid 1-chloro-ethyl ester,
pp) 3(S)-[tert-butoxycarbonylamino]-1-[1-chloroethyloxycarbonyl]pyrrolidine,
qq) 2(S)-[tert-butoxycarbonylaminomethyl]-1-[1-chloroethyloxycarbonyl]pyrrolidine,
rr) [N-methyl-N-2-(tert-butoxycarbonylmethylamino)-1,2-trans-cyclohexan-1-yl]carbamic acid 1-chloro-ethyl ester, The compounds of formula (II) are well known azole antifungals and commercially available (e.g. Prepn. of 1-[2-(2,4-Dichlorophenyl)-2-[(2,4-dichlorophenyl)methoxy]ethyl]-1H-imidazole: E. F. Godefroi et al., J. Med. Chem. 12, 784 (1969); Prepn. of cis-1-Acetyl-4-[4-[[2-(2,4-dichlorophenyl)-2-(1H-imidazol-1-ylmethyl)-1,3-dioxolan-4-yl]methoxy]phenyl]piperazine: J. Heeres et al., Ger. Pat. 2,804,-096; Prepn. of 4-[4-[4-[4-[[2-(2,4-Dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-[1,2,4]triazol-3-one: J. Heeres, L. J. J. Backx, Eur. Pat. Appl. 6,711; Prepn. of 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone: A. Tasaka et al., Chem. Pharm. Bull. 45, 321-326, 1997; Prepn. of (+)-2-(2,4-Difluorophenyl)-3-methyl-1-(1H-1,2,4-triazol-1-yl)-3-(6-(1H-1,2,4-triazol-1-yl)pyridazin-3-ylthio)butan-2-ol: T. Kai et al., Chem. Pharm. Bull. 44 (3), 568-571, 1996; Prepn. of (2R)-2-(2,4-diflourophenyl)-1-[3-[(E)-4-(2,2,3,3-tetrafluoropropoxy)-styryl]-(1,2,4-triazol-1-yl)-3-(1,2,4-triazol-1-yl)]propan-2-ol: H. Yamada et al., Antimicrob. Agents Chemother. 37 (11), 2412-2417, 1993; Prepn. of dl-Threo-2-(2,4-difluorophenyl)-3-methyl-sulfonyl-1-(1H-1,2,4-triazol-1-yl)-butan-2-ol: Drugs Future, 17, 1145-1146, 1992; Prepn. of (−)-4-[4-[4-[[5-(2,4-Difluorophenyl)-5-(1H-1,2,4-triazol-1-ylmethyl)tetrahydro-furan-3-yl]methoxy]phenyl]piperazinyl]phenyl]-2[(1S,2S)-1-ethyl-2-hydroxypropyl]-3H-1,2,4-triazol-3-one: Curr. Pharm. Des., 2, 209-224, 1996; Prepn. of (2R,3R)-3-[4-(4-cyanophenyl)thiazol-2-yl)]-2-(2,4-difluorophenyl)-1-(1H-1,2,4-triazol-1-yl)-butan-2-ol: Eisai Co. Ltd., EP 667346; Prepn. of 3-Methyl-3-methylthio-1-(1,2,4-triazol-1-yl)-2-(trifluoromethylphenyl)-butan-2-ol: S. S. Pharmaceutical Co. Ltd., EP 435081.

Other azoles of formula (II) as well as salts, hydrates or solvates thereof, like 3-fluoro, 2,5-difluoro- and 2,4,5-trifluoro-derivatives, can be manufactured according to the following synthetic scheme A, starting from 4-[(2R)-2-(3,4,5,6-tetrahydro-2H-pyran-2-yloxy)propionyl]morpholine [which can be prepared by a same procedure as described in Chem. Pharm. Bull. 41, 1035, 1993.]. This synthesis route has been described for example in European Patent Application No. 99101360.8.

Scheme A.:

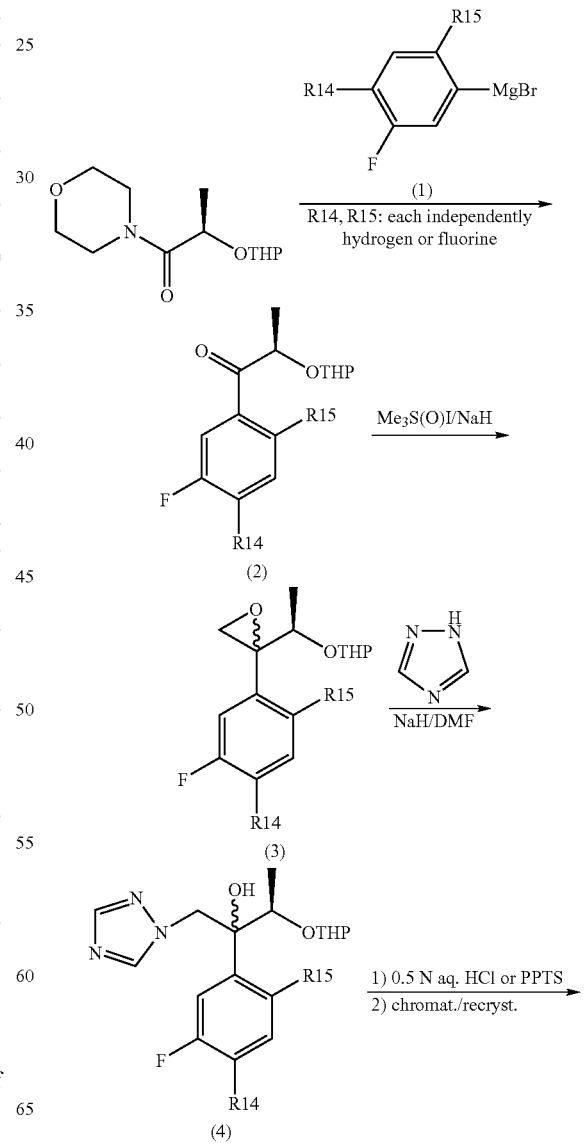

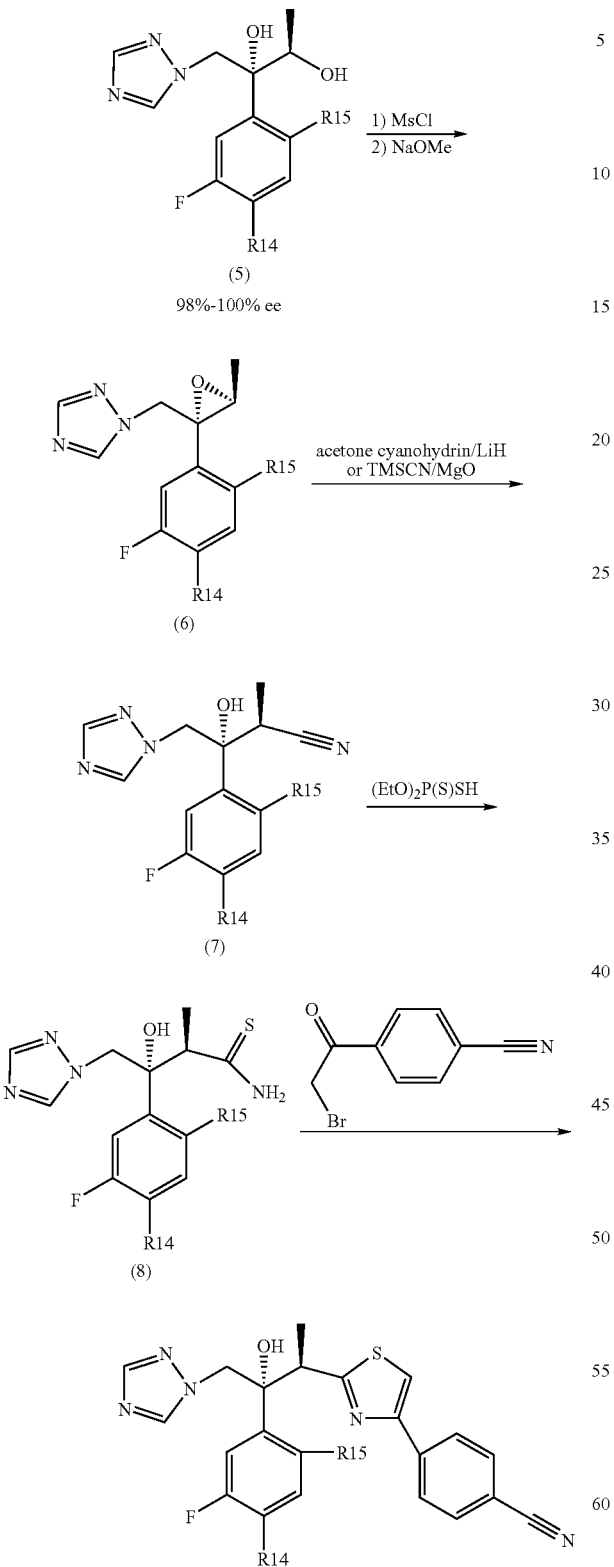

(THF) at a temperature between −10° C. and room temperature for 3 to 8 hr. to give a compound of the formula (2),

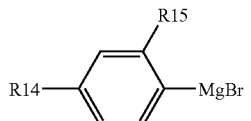

(1)

in which $R^{14}$ and $R^{15}$ are each independently for example hydrogen or fluorine (hereinafter $R^{14}$ and $R^{15}$ have the same meaning), followed by (b) reacting a compound of the formula (2) with trimethyl sulfoxonium iodide, in the presence of sodium hydride in THF and dimethyl sulfoxide (DMSO) or in the presence of BuLi in THF and N,N'-dimethylpropylene urea (DMPU), at a temperature between −5° C. and room temperature for 2 to 8 hr. to give a compound of the formula (3),

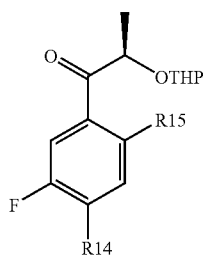

(3)

followed by (c) reacting a compound of the formula (3) with triazole in the presence of sodium hydride in dry dimethylformamide (DMF) at a temperature between 50° C. and 100° C. for 6 to 12 hr. to give a compound of the formula (4),

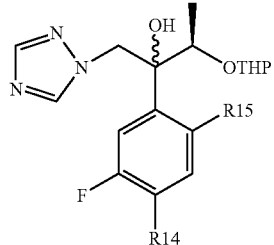

(4)

(a) Reacting 4-[(2R)-2-(3,4,5,6-tetrahydro-2H-pyran-2-yloxy)propionyl]morpholine with a compound of the formula (1) in an organic solvent such as tetrahydrofuran followed by (d) reacting a compound of the formula (4) with aqueous hydrochloric acid at a concentration between 1N and 0.1N solution, in methanol and n-hexane at room temperature or pyridinium p-toluenesulfonate in ethanol, at a temperature between room temperature and 100° C. for 2 to 6 hr. The resulting compound is recrystalized from t-butyl methyl ether and n-hexane to give a compound of the formula (5), (5)

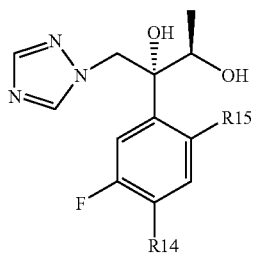

followed by (e) reacting a compound of the formula (5) with mesyl chloride in $CH_2Cl_2$ and methyl acetate (AcOEt) in the presence of an organic base such as triethylamine or pyridine for 30 min. to 2 hr. This reaction is followed by epoxy ring formation with sodium methoxide in methanol for 15 min. to 1 hr. The resulting compound is purified by recrystalization from t-butyl methyl ether and n-hexane or by silicagel column chromatography using $CH_2Cl_2$ and methanol as eluent, to give a compound of the formula (6), (6)

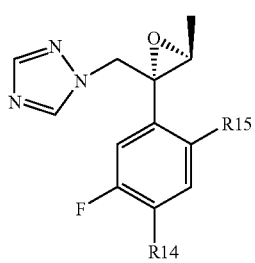

followed by (f) reacting a compound of the formula (6) with acetone cyanohydrin in the presence of lithium hydride in THF under reflux for 4 to 8 hr or trimetylsilyl cyanide in the presence of magnesium oxide in o-xylene at a temperature between 100° C. and 160° C. for 20 to 40 hr, then removing of trimethylsilyl group with conc. hydrogen chloride solution in THF to give a compound of the formula (7), (7)

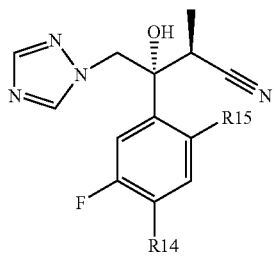

followed by (g) reacting a compound of the formula (7) with dithiophosphoric acid O,O-diethyl ester and water or dithiophosphoric acid O,O-diethyl ester, water and iso-propanol at a temperature between 90° C. and 150° C. for 4 to 8 hr. to give a compound of the formula (8), (8)

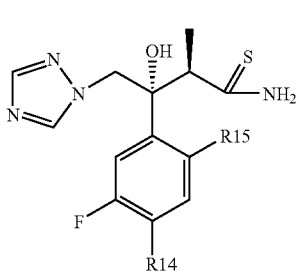

followed by (h) reacting a compound of the formula (8) with 2-bromo-4'-cyanoacetophenone at a temperature between room temperature and 80° C. in acetonitrile, ethanol or methanol for 2 to 24 hr. to give a compound of the formula (II), The compounds of the formula (IV) and (V) can be prepared by procedures similar to those known in the art. The typical example of the reaction is disclosed in Example 1 [scheme(1)], Example 2[scheme(2)], Example 3[scheme (3)], or Example 4[scheme(4)]. In these examples, each starting material [(a), (d), (i), (n) or (r)] was purchased from TOKYO CHEMICAL INDUSTRY CO., LTD (1-13-6 Nihonbashi Muromachi, Chuo-ku, Tokyo 103, Japan). Other starting materials are known in the art and/or commercially available.

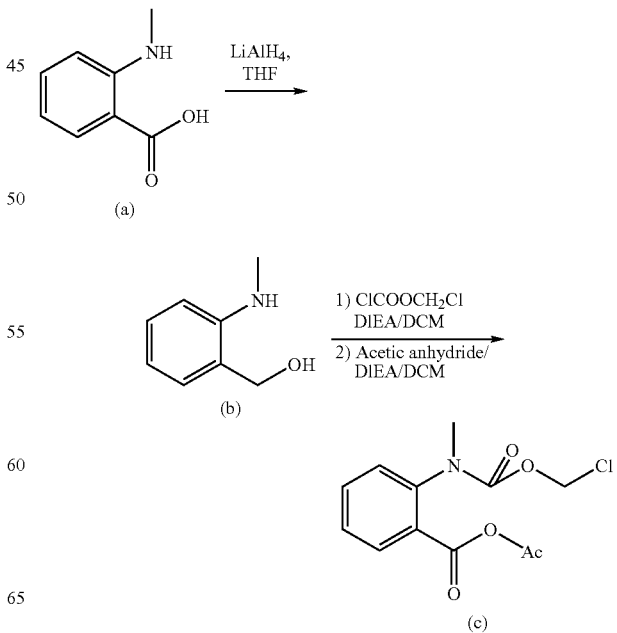

Scheme (2)
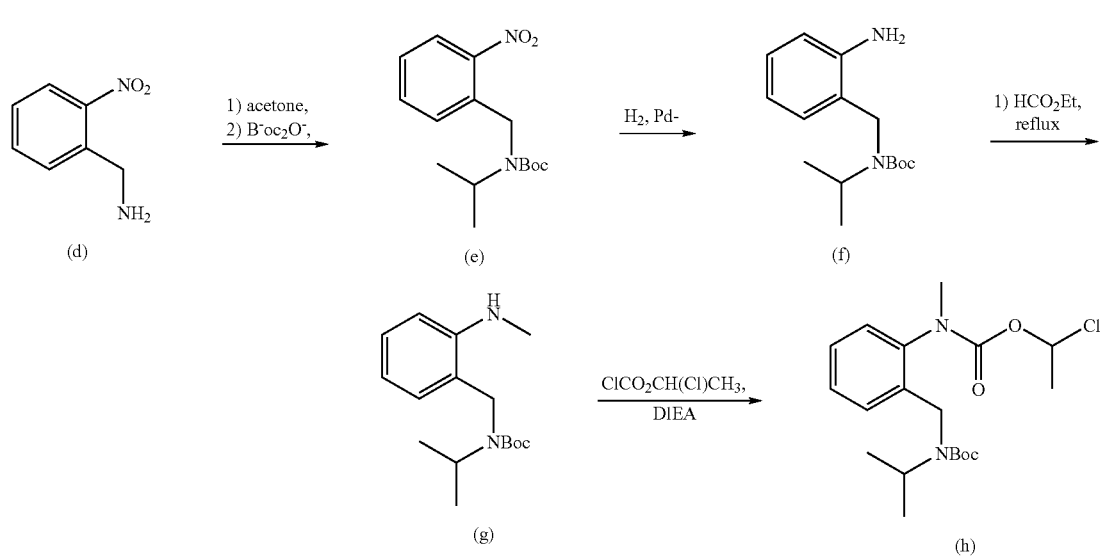
Scheme (3)
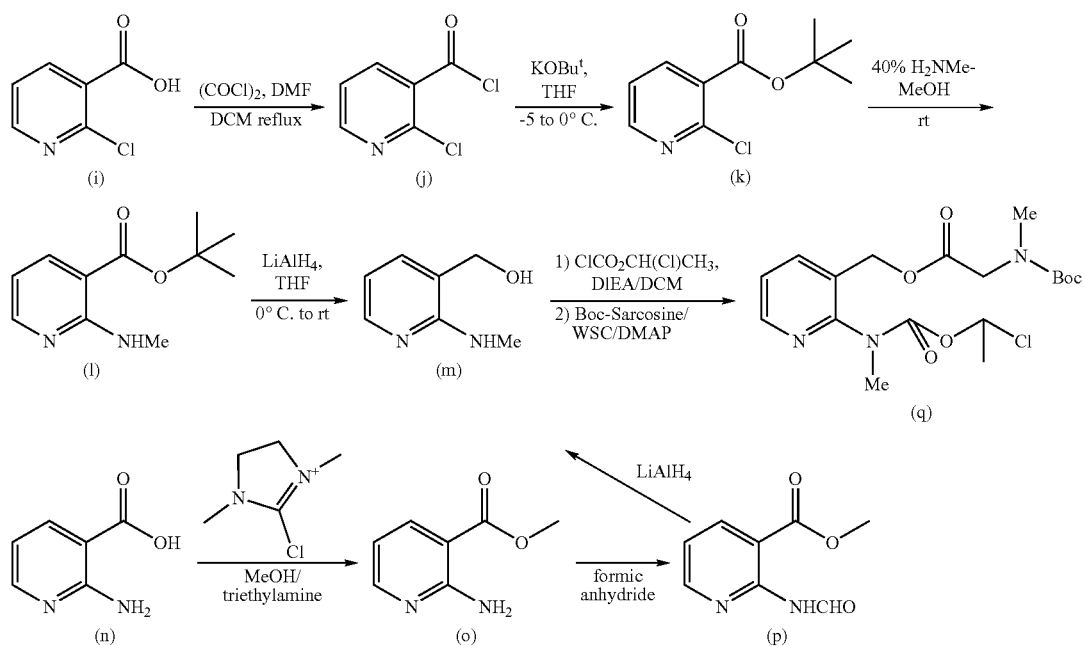
Scheme (4)
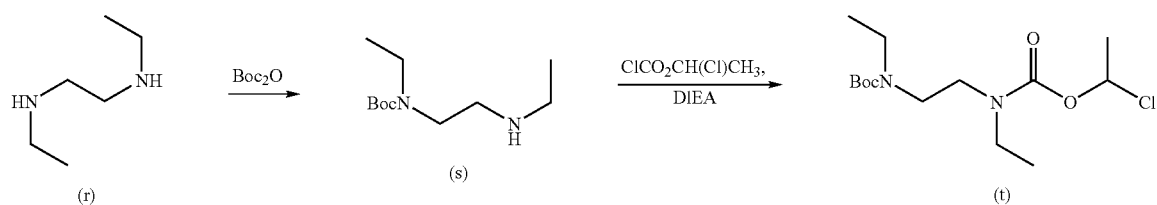

Accordingly, the present invention also refers to a process for the manufacture of a compound of the general formula (I) as defined above, which comprises reacting an azole compound possessing antifungal activity of the general formula (II) as defined above, with a compound of the general formula (IV) as defined above.

Further, the invention comprises a process for the manufacture of a compound of formula (III) as defined above as well as salts, hydrates of solvates thereof, which comprises reacting an azole compound possessing antifungal activity of the general formula (II) as defined above with a compound of general formula (V) as defined above.

The typical example of the reaction of a compound of the formula (II) with the compound of the formula (IV) or (V) is disclosed in Example 5[scheme(5)], Example 6[scheme(6)], Example 7[scheme(7)] or Example 8[scheme(8)]. In these Examples, the compounds were synthesized by procedures known to those skilled in the art which are described for example in European Patent Application No. 99101360.8.

The quarternarization reaction can be carried out in a solvent such as methylene chloride, chloroform, benzene, toluene, acetonitrile, tetrahydrofuran, dioxane, or dimethylformamide, preferably chloroform, acetonitrile, or dimethylformamide.

The reaction time in the above quarternarization reaction may be varied within a relatively wide range. In general, the reaction can be carried out at a temperature between 0° C. and 100° C., preferably between 0° C. and 50° C.

Preferably, an amino group present in $R^6$ in the compound of formula (V) or an amino group present in $R^3$ in the compound of formula (IV) are protected by a suitable amino protecting group as tert-butoxy carbonyl.

The protecting group may, if necessary, be removed after the quarternarization reaction as disclosed in Example 6[scheme(6)], Example 7[scheme(7)] or Example 8[scheme(8)] by procedures known to those skilled in the art.

Scheme (5)

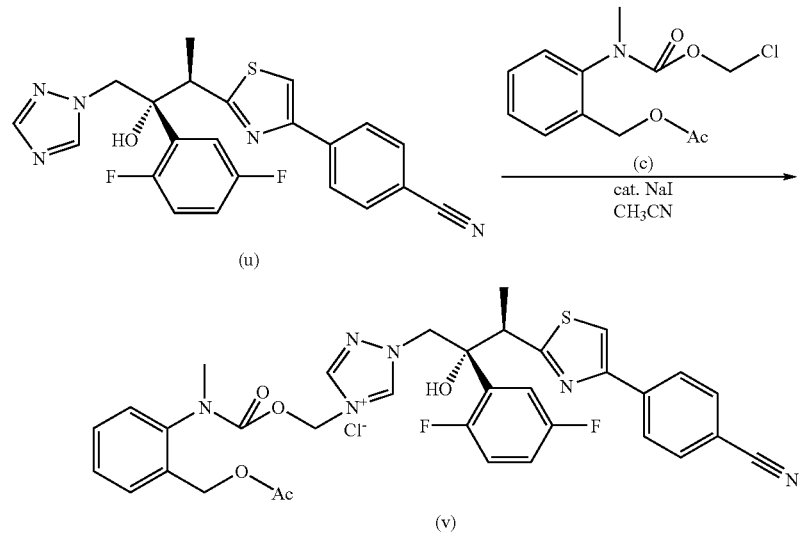

Scheme (6)

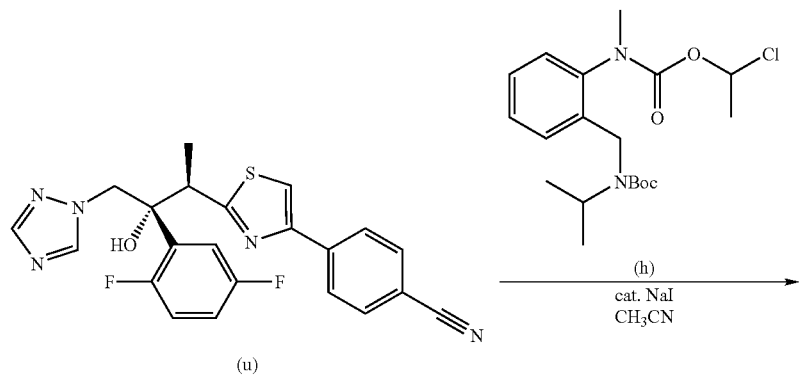

-continued
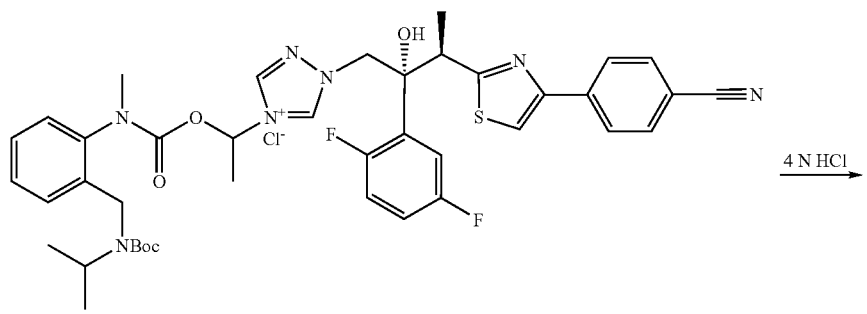
(w)
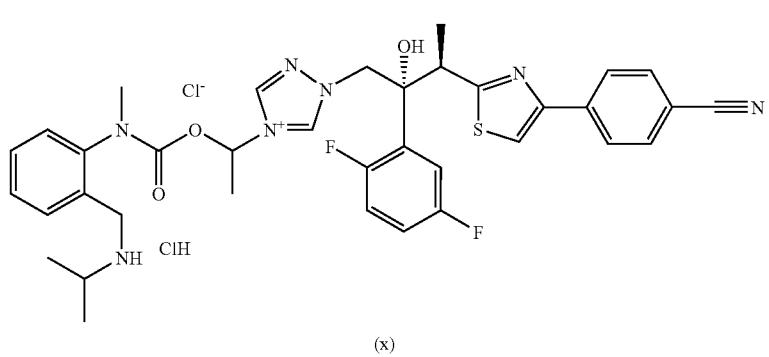
(x)
Scheme (7)
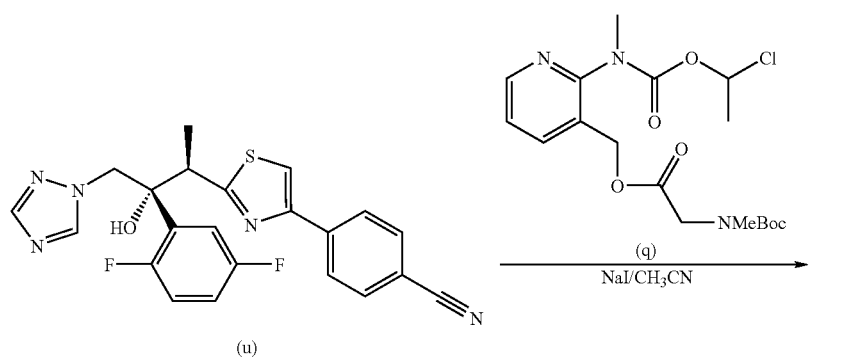
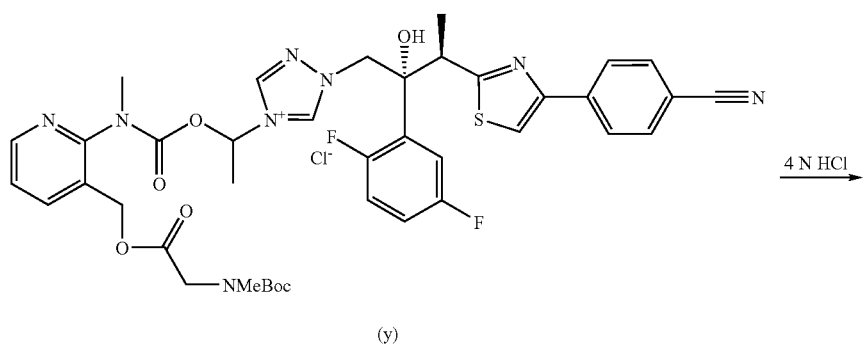
(y)

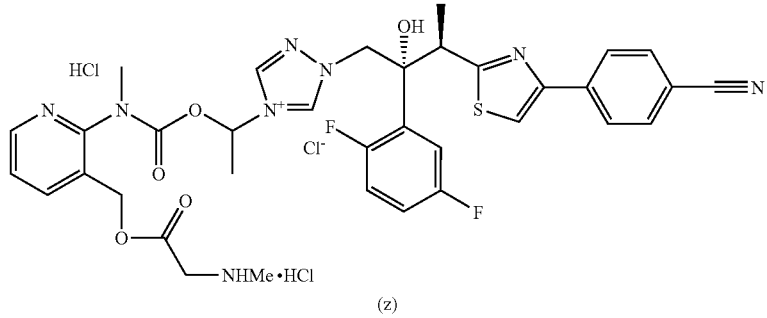

(z)

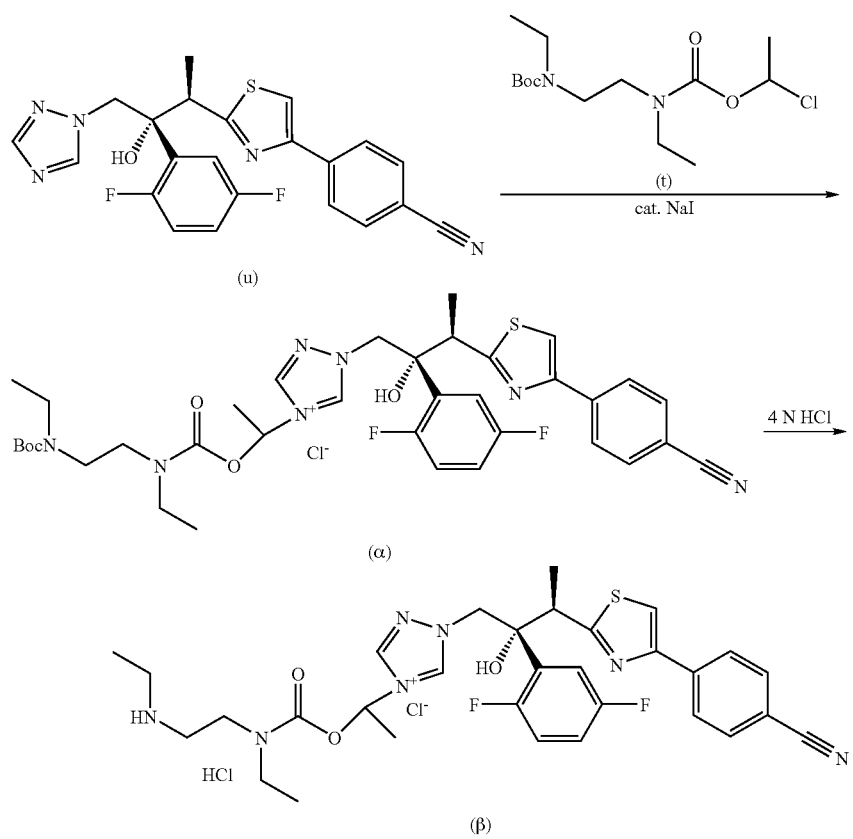

The compounds of the formula (I) may contain an amino acid ester substituent and/or other basic amino groups which may form acid addition salts. The term "salts of compounds of the formula (I)" refers to such acid addition salts. These salts may be derived from pharmaceutically acceptable acids as described earlier with reference to the Symbol X⁻. The salt formation can be performed when removing a protecting group, or can be performed ad hoc by procedures known per se.

The hydration can be effected in the course of the manufacturing process or can occur gradually as a result of hygroscopic properties of an initially anhydrous product. Solvates with pharmaceutically acceptable solvents such as ethanol can be obtained for example, during precipitation.

The present invention also refers to the above compounds of formula (I) as obtained by a process as described above and to a pharmaceutical composition, in particular for use as an antifungal, comprising a compound as defined above and a pharmaceutically acceptable carrier.

Further the present invention is directed to a method of treating fungal infections comprising administering to the infected organism an effective amount of a compound as defined above, to the compounds as defined above for use as therapeutic active substances, in particular as antifungallly active substances, and to the use of a compound as defined above for the preparation of a medicament for the prophylaxis and/or treatment of fungal infections. Such a medicament comprises a compound as defined above.

The novel azole compounds represented by the formula (I) as well as hydrates or solvates thereof have much higher water solubility than known antimycotic azole compounds represented by the formula (II) (see Table 1).

TABLE 1

| Solubility | | |
|---|---|---|
| Compound (Example No.) | Solubility (mg/ml) | Solvent |
| 5 | 1 | a |
| 6 | >10 | a |
| 7 | >1000 | a, b |
| 8 | >10 | a |
| 6.1. | >10 | a |
| 6.2. | >10 | a |
| 7.10. | >10 | a |
| 7.15. | >10 | a |
| 7.20. | >30 | a |
| 7.21. | >10 | a |
| 8.5. | >10 | a |

* solvent a = distilled water, solvent b = physiological saline

In addition, the novel azole compounds of the formula (I) are chemically stable in aqueous solution at room temperature more than three days, but are efficiently converted into compounds of the formula (II) in either mouse, rat, monkey or human plasma.

The conversion of representatives of the new azole compounds of the formula (I) to (2R,3R)-3-[4-(4-cyanophenyl)thiazol-2-yl)]-2-(2,5-difluorophenyl)-1-(1H-1,2,4-triazol-1-yl)-butan-2-ol, in human plasma are shown in Table 2.

The compounds of formula were incubated with human plasma at a concentration of 10 μg/ml at 37° C. for up to 120 min. After quenching by the addition of EtOH, conversion half-life was determined by HPLC-MASS analysis (see Example D).

TABLE 2

Conversion of the new azole compounds to (2R,3R)-3-[4-(4-cyanophenyl)thiazol-2-yl)]-2-(2,5-difluorophenyl)-1-(1H-1,2,4-triazol-1-yl)-butan-2-ol(u) in plasma

| Example No | Cnversion to (2R,3R)-3-[4-(4-cyanophenyl)thiazol-2-yl)]-2-(2,5-difluorophenyl)-1-(1H-1,2,4-triazol-1-yl)-butan-2-ol(u) in plasma |
|---|---|
| 5 | <2 min in rat plasma |
| 7 | <2 min in human plasma |
| 7.3. | 6 min in human plasma |
| 7.4. | 2 min in human plasma |
| 7.10. | 3 min in human plasma |
| 7.13. | 2 min in human plasma |

In vivo efficacy of the compounds of the present invention is shown in table 3. Male Fisher rats, strain F344/DuCrj, were employed for experimental infection models such as systemic candidiasis, systemic aspergillosis and pulmonary aspergillosis model. Immunocompetent 4 weeks old rats were used for systemic candidiasis or systemic aspergillosis which occurred after infection with *Candida albicans conidia* of $5 \times 10^6$/rat or with *Aspergillus fumigatus conidia* of $6 \times 10^5$/rat via tail vein. Otherwise for pulmonary aspergillosis model, rats had been immunosuppressed with cortisone acetate treatments prior to infection with $2 \times 10^5$/rat intratrachially. Treatments were given twice on the first day and once daily on following 4 days both for systemic and pulmonary aspergillosis (lb.i.+4q.d.), for systemic candidiasis rats were treated at 0, 4, 24, and 48 h after infection (lb.i.d.+2q.d.). Effective dose 50% (ED50) values were determined on day 14 after infection.

TABLE

| in vivo efficacy (μmol/kg) | | | | | |
|---|---|---|---|---|---|
| | Systemic Fluconazole resistance candidiasis | | Pulmonary aspergillosis | | Systemic aspergillosis |
| | p.o. | i.v. | p.o. | i.v. | p.o. | i.v. |
| Example 7 | 14.1 | 13.3 | | | 8.8 | 13.5 |
| Itraconazole | | | | | 4.9 | |
| Fluconazole | 21.8 | | | | | |

| | | Rat systemic mycosis[ED50(μmol/kg) on day14] | | | | | |
|---|---|---|---|---|---|---|---|
| | | C. albicans CY1002 | C. albicans CY3003 | C. parapsilosis KULM219C | C. tropicalis CY5042 | FCZ$^R$- C. albicans UTHS93-2067 | A. fumigatus CF1003 |
| Example 7 | I.V. | 4 | 1.6 | 7.6 | 1 | 2.8 | 11 |
| | PO. | 4 | 2.5 | 6.5 | 1 | 7 | 9 |
| Fluconazole | PO. | 1.9 | 1 | 17 | 2 | 8.1 | 94 |
| Itraconazole | PO. | 4.7 | 2.3 | 20 | 2 | 4.2 | 8.9 |

Therefore, the water soluble azole antifungal agents, represented by the formula (I) as well as salts, hydrates or solvates thereof, according to the present invention, exhibit potent antifungal activity against various fungal infections including Aspergillosis in mice over a very wide range of dosages both orally and parenterally and are useful as antifungal agents.

The present invention further relates to the pharmaceutical compositions containing the azole compound of the formula (I) as well as salts, hydrates or solvates thereof and pharmaceutically acceptable carrier.

The azole compounds of the formula (I) as well as salts, hydrates or solvates thereof are active against a variety of fungal species including *Candida* spp., *Cryptotoccus neoformans, Aspergillus* spp., *Trichophyton* spp., *Microsporum* spp., *Exophiala* spp., *Blastomyces dermatitidis,* and *Histoplasma capsulatum*.

Thus, the compounds of the present invention are useful for topical and systemic treatment of mycoses in animals as well as in humans. For example, they are useful in treating topical and mucosal fungal infections caused by, among other genera, *Candida, Trichophyton,* or *Microsporum*. They may also be used in the treatment of systemic fungal infections caused by, for example, *Candida* spp., *Cryptococcus neoformans, Aspergillus* spp., *Paracoccidiodes* spp., *Sporotrix* spp., *Exophiala* spp., *Blastomyces* spp., or *Histoplasma* spp.

For clinical use, the azole compounds of the formula (I) as well as salts, hydrates or solvates thereof can be administered alone, but will generally be administered in pharmaceutical admixture formulated as appropriate to the particular use and purpose desired, by mixing excipient, binding agent, lubricant, disintegrating agent, coating material, emulsifier, suspending agent, solvent, stabilizer, absorption enhancer and/or ointment base. The admixture can be used for oral, injectable, rectal or topical administration.

Pharmaceutical formulation for oral administration may be granule, tablet, sugar coated tablet, capsule, pill, suspension or emulsion. For parenteral injection, for example, intravenously, intramuscularly or subcutaneously, the azole compounds of formula (I) may be used in the form of a sterile aqueous solution which may contain other substances, for example, salts or glucose to make the solution isotonic. The azole compounds can also be administered in the form of a suppository or pessary, or they may be applied topically in the form of a lotion, solution, cream, ointment or dusting powder.

The daily dosage level of the azole compounds of the formula (I) is from about 0.1 to about 50 mg/kg (in divided doses) when administered in one, two or more dosages by either the oral or parenteral route. Thus tablets or capsules of the compounds may contain from about 5 mg to about 0.5 g of active compound for administration. In any event the actual dosage can be determined by the physician and it may be varied upon the age, weight and response of the particular patient.

In addition, the azole compounds of the formula (I) as well as salts, hydrates or solvates thereof have activity against a variety of plant pathogenic fungi, including for example *Pyricularia oryzae, Pythium aphanidermatum, Alternaria* spp., and *Paecilomyces variotii*.

Thus, they can be applied for agricultural and horticultural purposes preferably in the form of a composition formulated as appropriate to the particular use and purpose desired, for example dusting powders, or granules, seed dressings, aqueous solutions, dispersions or emulsions, dips, sprays or aerosols. Such compositions may contain such conventional carriers, diluents or adjuvants as are known and acceptable in agriculture and horticulture. Other compounds having herbicidal or insecticidal, or additional antifungals can be incorporated in the compositions. The compounds and compositions can be applied in a number of ways, for example they can be applied directly to the plant foliage, stems, branches, seeds or roots or to the soil or other growing medium, and they may be used not only to eradicate the disease, but also prophylactically to protect the plants or seeds from attack.

The following examples illustrate the preferred methods for the preparation of the compounds of the present invention, which are not intended to limit the scope of the invention thereto.

EXAMPLES

Example 1

[N-methyl-N-2-(acetoxymethyl)phenyl]carbamic acid chloromethyl eter a) Preparation of 2-(N-methylamino)-benzylalcohol To a suspension of lithium aluminum hydride (0.76 g, 0.02 mol) in dry tetrahydrofuran (40 ml) was added a solution of N-methylanthranilic acid(a) (1.51 g, 0.01 mol) in dry tetrahydrofuran under Ar atmosphere. After refluxing for 1 h, the reaction was quenched by adding ice water (50 ml). The mixture was filtered on a celite pad and thoroughly washed with dichloromethane (50 ml). The organic layer was separated and the water layer was extracted with dichloromathane (50 ml). The combined organic layer was washed with brine (30 ml), dried over anhydrous sodium sulfate and concentrated under reduced pressure. The resulting yellowish oil was purified on a column of silica gel (wakogel C-200 50 g, eluent n-hexane:ethyl acetate=2:1) to give the title compound(b) as colorless oil (1.18 g, 86%). $^1$H-NMR (270 MHz, CDCl$_3$): δ 2.87 (3H, s), 3.00-3.10 (1H, br.s), 4.64 (2H, s), 6.65-6.69 (2H, m), 7.05 (1H, d, J=7.2), 7.23-7.29 (1H, m)

b) Preparation of [N-methyl-N-2-(acetoxymethyl)phenyl]carbamic acid chloromethyl ester Step 1

To a solution of 2-(N-methylamino)-benzylalcohol(b) (536 mg, 3.9 mmol) in dry dichloromethane (25 ml) and diisopropylethylamine (681 μl, 3.9 mmol) was added dropwise chloromethyl chloroformate (360 μl, 4.0 mmol) and the reaction mixture was stirred at 0° C. with occasional check of the reaction progress by t.l.c (n-hexane:ethyl acetate=2:1). After 2 h, the starting material disappeared on t.l.c and the solution was used directly for the following reaction.

Step 2

To the reaction mixture were added diisopropylethylamine (900 μl, 5.0 mmol) and acetic anhydride (400 mg) and stirred for 3 h at ambient temperature. The reaction mixture was partitioned with dichloromethane (50 ml) and water (30 ml). The water layer was separated and extracted again with dichloromethane (50 ml). The combined organic layer was washed with brine (30 ml×2), dried over anhydrous sodium sulfate and concentrated under reduced pressure. The resulting yellowish oil was purified on a column of silica gel (wakogel C-200 10 g, eluent dichloromethane:methanol=200:1) to give the title compound(c) as colorless syrup (740 mg, 70%). EI-MS: m/z 271 (M$^+$); $^1$H-NMR (270 MHz, CDCl$_3$): δ 2.10 (3H, s), 3.30 (3H, s), 5.07-5.78 (2H, br.d), 5.60 (0.8H, d, J=5.9), 5.73 (0.8H, d, J=5.9), 5.85 (0.4H, br.s), 7.16-7.23 (1H, m), 7.37-7.49 (3H, m).

The following compounds in Example 1.1.-1.7. were obtained according to a manner analogous to those of Example 1.

1.1.

[N-methyl-N-phenyl]carbamic acid chloromethyl ester. Physical form: colorless oil; LC-MS: m/z 200 (M+1)$^+$; $^1$H-NMR(CDCl$_3$): δ 3.35 (s, 3H), 5.76 (bs, 2H), 7.19-7.43 (m, 5H).

1.2.

[N-methyl-N-3-(acetoxymethyl)pyridin-2-yl]carbamic acid 1-chloro-ethyl ester. Physical form: colorless oil; LC-MS: m/z 287(M+1)+; $^1$H-NMR(CDCl$_3$): δ 1.60(3H, br.s), 2.12(3H, s), 3.35(3H, br.s), 5.10(2H, m), 6.57(1H, m), 7.30 (1H, m), 7.82(1H, m), 8.46(1H, m).

1.3.

[N-acety-N-methyl]carbamic acid 1-chloro-ethyl ester. Physical form: colorless oil; LC-MS: m/z 180(M+1)+; $^1$H-NMR(CDCl$_3$): δ 1.89(3H, d, J=5.6 Hz), 2.56(3H, s), 3.22 (3H, s), 6.57(1H, q, J=5.6 Hz).

1.4.

2(S)-[acetoxymethyl]-1-[chloromethyloxycarbonyl]pyrrolidine. Physical form: colorless oil; LC-MS: m/z 236(M+ 1)+.

1.5.

[N-methyl-N-acetoxyethyl]carbamic acid chloromethyl ester. Physical form: yellow oil; LC-MS: m/z 210(M+1)+; $^1$H-NMR(CDCl$_3$): δ2.08(3H, s), 3.01 (3H, m), 3.57(2H, m), 4.17-4.41(2H, m), 5.76(2H, br.s).

1.6.

[N-methyl-N-3-(acetoxy)propyl]carbamic acid chloromethyl ester. Physical form: colorless oil; LC-MS: m/z 224(M+ 1)+; $^1$H-NMR (CDCl$_3$): δ 1.82-1.98(2H, m), 2.06(3H, s), 2.96(3H, d, J=8.6 Hz), 3.32-3.46(2H, m), 4.09(2H, t, J=6.0 Hz), 5.78(2H, s).

1.7.

[N-2-(methyl)phenyl-N-acetoxyethyl]carbamic acid chloromethyl ester. Physical form: yellow oil; LC-MS: m/z 286 (M+1)+; $^1$H-NMR (CDCl$_3$): δ 1.99 (s, 3H), 2.24 (s, 3H), 3.62-3.69 (m, 1H), 4.04-4.29 (m, 3H), 5.58 (d, J=5.9 Hz, 1H), 5.79 (d, J=5.9 Hz, 1H), 7.12-7.28 (m, 4H).

Example 2

[N-methyl-N-2-((tert-butoxycarbonylisopropylamino)methyl)phenyl]carbamic acid 1-chloro-ethyl ester a) Preparation of Isopropyl-(2-nitro-benzyl)-carbamic acid tert-butyl ester To a mixture of 2-nitrobenzylamine hydrochloride (500 mg, 2.65 mmol) and acetone (0.39 ml, 5.30 mmol) in methanol (13 ml) was added sodium cyanoborohydride (500 mg, 7.95 mmol) at 0° C. The temperature was warm up to room temperature. After stirring for 3 hr, the mixture was concentrated in vacuo and extracted with dichloromethane. The combined organic phase was washed with water and brine, dried over anhydrous magnesium sulfate, filtered and concentrated in vacuo to give N-isopropyl-2-nitrobenzylamine as yellow oil. This compound was used in next step without further purification.

To a mixture of N-isopropyl-2-nitrobenzylamine and N,N-diisopropylethyl amine (1.15 ml, 6.63 mmol) in tetrahydrofuran (20 ml) was added di-tert-butyl dicarbonate (1.22 ml, 5.30 mmol) at room temperature. After stirring overnight, the mixture was quenched with water and extracted with ethyl acetate. The combined organic phase was washed with water and brine, dried over anhydrous magnesium sulfate, filtered and concentrated in vacuo. The residue was purified by column chromatography (15% ethyl acetate-hexane) to afford isopropyl-(2-nitro-benzyl)-carbamic acid tert-butyl ester (e) (736 mg, 2.50 mmol, 94%) as light yellow oil.

b) Preparation of (2-Amino-benzyl)-isopropyl-carbamic acid tert-butyl ester

To a solution of isopropyl-(2-nitro-benzyl)-carbamic acid tert-butyl ester (730 mg, 2.48 mmol) in ethyl acetate (10 ml) was added acetic acid (0.156 ml, 2,73 mmol) and catalytic amount of palladium 10 wt. % on activated carbon. The mixture was stirred overnight under hydrogen atmosphere. The mixture was filtered and concentrated in vacuo. The residue was purified by column chromatography (15% ethyl acetate-hexane) to afford (2-amino-benzyl)-isopropyl-carbamic acid tert-butyl ester (f) (568 mg, 2.15 mmol, 87%) as reddish oil.

c) Preparation of Isopropyl-(2-methylamino-benzyl)-carbamic acid tert-butyl ester (2-Amino-benzyl)-isopropyl-carbamic acid tert-butyl ester (f) (552 mg, 2.09 mmol) was dissolved into ethyl formate (10 ml). The solution was stirred overnight at 70° C. The solvent was removed in vacuo to give N-formate as red oil. This compound was used in next step without further purification.

Lithium aluminum hydride (79 mg, 2.09 mmol) was suspended in tetrahydrofuran (5 ml). A solution of N-formate in tetrahydrofuran (5 ml) was added gently dropwise to a suspension of lithium aluminum hydride. After stirring for 30 min, ammonium chloride solution was slowly added to quench the reaction. The reaction mixture was filtered and concentrated in vacuo. The crude product was purified by column chromatography (10% ethyl acetate-hexane) to afford Isopropyl-(2-methylamino-benzyl)-carbamic acid tert-butyl ester (g) (126 mg, 0.453 mmol, 22%).

d) Preparation of [N-methyl-N-2-((tert-butoxycarbonylisopropylamino)methyl)phenyl]carbamic acid 1-chloro-ethyl ester To a solution of isopropyl-(2-methylamino-benzyl)-carbamic acid tert-butyl ester (119 mg, 0.428 mmol) and N,N-diisopropylethylamine (0.97 ml, 0.556 mmol) in dichloromethane (4 ml) was added chloroethylchloroformate (0.055 ml, 0.514 mmol) at 0° C. The reaction temperature was warm up to room temperature. After stirring for 15 min, the reaction mixture was quenched with water and extracted with dichloromethane. The combined organic phase was washed with water and brine, dried over anhydrous magnesium sulfate, filtered and concentrated in vacuo. The crude product was purified by column chromatography (20% ethyl acetate-hexane) to afford [N-methyl-N-2-((tert-butoxycarbonylisopropylamino)methyl)phenyl]carbamic acid 1-chloro-ethyl ester as colorless oil (158 mg, 0.409 mmol, 96%). Physical form: colorless oil; EI-MS: m/z 384(M+); $^1$H-NMR (CDCl$_3$): δ 0.93~1.12(6H, m), 1.16~1.60(12H, m), 3.20(3H, s), 4.02~4.58(3H, m), 6.49~6.67(1H, m), 6.98~7.31 (4H, m).

The following compounds in Example 2.1.-2.3. were obtained according to a manner analogous to those of Example 2.

2.1.

[N-2-[(tert-butoxycarbonylisopropylamino)methyl]phenyl]carbamic acid 1-chloro-ethyl ester. Physical form: colorless oil; LC-MS: m/z 371 (M+1)+.

2.2.

[N-2-[(tert-butoxycarbonyl-pentan-3-ylamino)methyl]phenyl]carbamic acid 1-chloro-ethyl ester. Physical form: colorless oil; LC-MS: m/z 399(M+1)$^+$.

2.3.

[N-methyl-N-2-[(tert-butoxycarbonylmethylamino)methyl]phenyl]carbamic acid 1-chloro-ethyl ester. Physical form: light yellow oil; LC-MS: m/z 357 (M+1)$^+$; $^1$H-NMR (CDCl$_3$): δ 1.22~1.71 (12H, m), 2.64~2.93 (3H, m), 3.21 (3H, s), 4.17~4.58 (2H, m), 6.49~6.63 (1H, m), 7.02~7.39(4H, m).

Example 3

[N-methyl-N-3-((tert-butoxycarbonylmethylamino)acetoxymethyl)pyridin-2-yl]carbamic acid 1-chloro-ethyl ester a) Preparation of 2-Chloronicotinoyl chloride To a suspension of 2-chloronicotinic acid (37.8 g, 0.240 mol) in dry DCM (150 mL) and DMF (0.1 mL) cooled in an ice-bath was added oxalyl chloride (22.9 mL, 0.264 mol) dropwise over a period of 15 min. After stirring for 1 h at 0° C., the reaction mixture was heated to reflux for 6 h (the mixture became a clear brownish solution). The solvent and the excess oxalyl chloride was evaporated under reduced pressure. Toluene (100 mL) was added to the residue and the mixture was evaporated. The obtaining residue was purified by vacuum distillation to give 2-chloronicotinoyl chloride (41.7 g, 99%); bp 98-100° C./2 mmHg, mp 38-39° C. (from Lancaster catalog). Caution: Distillation may need a special care due to the high melting point of the product.

b) Preparation of t-Butyl 2-chloronicotinate

A solution of 2-chloronicotinoyl chloride (41.7 g, 0.237 mol) in dry THF (400 mL) was cooled in an ice-EtOH-water bath (−5° C.). KOBu$^t$ (27.9 g, 0.249 mol) was added portionwise over a period of 30 min and the mixture was stirred for 2 h at 0° C. THF was evaporated under reduced pressure, and the residue was extracted with EtOAc (600 mL). The EtOAc layer was washed with water and brine, dried over MgSO$_4$, and evaporated under reduced pressure. The obtaining residue was purified by a short silica gel column chromatography (ca. 100 g of silica gel, eluent:EtOAc/hexane=1/1) to give t-butyl 2-chloronicotinate (49.0 g, 97%) as an oil; $^1$H NMR (CDCl$_3$): δ 1.64 (s, 9H), 7.32 (dd, J=4.6 and 7.6 Hz, 1H), 8.06 (dd, J=2.0 and 7.6 Hz, 1H), 8.48 (dd, J=2.0 and 4.6 Hz, 1H).

c) Preparation of t-Butyl 2-(N-methylamino)nicotinate t-Butyl 2-chloronicotinate(k) (50.0 g, 0.234 mol) was dissolved in a 40% methylamine-methanol solution (300 mL) and the mixture was stirred at room temperature for 30 h. The mixture was evaporated under reduced pressure and the resulting residue was dissolved in EtOAc (750 mL). The EtOAc solution was washed with water, dried over MgSO$_4$ and evaporated under reduced pressure. The obtaining oily crude product was purified by a short silica gel column chromatography (ca. 300 g of silica gel, eluent:EtOAc/hexane=1/3) to give t-butyl 2-(N-methylamino)nicotinate(l) (45.0 g, ca. 92%) contaminated by starting meterial; $^1$H NMR (CDCl$_3$): δ 1.57 (s, 9H), 3.05 (d, J=5.0 Hz, 3H), 6.49 (dd, J=4.6 and 7.6 Hz, 1H), 7.96 (bs, 1H), 8.04 (dd, J=2.0 and 7.6 Hz, 1H), 8.28 (dd, J=2.0 and 4.6 Hz, 1H).

d) Preparation of 3-Hydroxymethyl-2-(methylamino)pyridine

To a solution of t-butyl 2-(methylamino)nicotinate (45.0 g, 0.216 mol) in dry THF (500 mL) cooled in an ice-bath was added LiAlH$_4$ (9.84 g, 0.259 mol) portionwise over a period of 30 min. After stiring for 1 h at 0° C., the mixture was warmed to room temperature and stirred for 2 h. After cooling in an ice-bath, the excess LiAlH$_4$ was decomposed completely by the careful addition of H$_2$O (10 mL) and 1N NaOH aqueous solution (10 mL). Na$_2$SO$_4$ (100 g) was added and the mixture was filtered through a pad of celite. The filtrate was evaporated under reduced pressure and the resulting residue was purified by column chromatography (400 g of silica gel, eluent:DCM/MeOH=20/1-10/1) to give the desire product which was further purified by recrystallization from DCM-hexane to give 3-hydroxymethyl-2-(N-methylamino)pyridine(m) (22.7 g, 76%); $^1$H NMR (CDCl$_3$): δ 2.30 (brs, 1H), 3.01 (d, J=4.6 Hz, 3H), 4.58 (s, 2H), 5.40 (brs, 1H), 6.50 (dd, J=5.1 and 7.3 Hz, 1H), 7.21 (dd, J=1.7 and 7.3 Hz, 1H), 8.08 (dd, J=1.7 and 5.1 Hz, 1H).

e) Preparation of Methyl 2-aminonicotinate

To a mixture of 2-aminonicotinic acid(n) (30.0 g 217 mmol) and 2-chloro1,3-dimethyl imidazolinium chloride (55.2 g 326 mmol) in MeOH (750 ml) was added dropwise triethylamine (91 ml 652 mmol). The resultant mixture was stirred at room temperature for 1 h. The mixture was then evaporated under reduced pressure to afford a residue. The residue was purified by extraction with ethyl acetate (300 ml×2). The combined organic phase was washed with water (200 ml×2) and brine (200 ml). Dried over anhydrous sodium sulfate, filtered and concentrated to give an essentially pure methyl 2-aminonicotinate (31.3 g, yield 94%). This compound was used in next step without further purification.

f) Preparation of Methyl N-formylaminonicotinate

Acetic formic anhydride (AFA) was generated in in the flask by dropwise addition of 98% formic acid (24.5 ml 650 mmol) to acetic anhydride (50.0 ml, 530 mmol) maintained at 0° C. followed by genntle heating (50° C., 2 h).

The mixture was cooled to room temperature. Methyl 2-aminonicotinate(o) (31.3 g, 206 mmol) was dissolved in dry THF (120 ml) and added to the mixture. The mixture was stirred overnight at room temperature and solvents was removed in vacuo to give an essentially pure methyl N-formylaminonicotinate(p) (37.0 g). This compound was used in next step without further purification.

g) Preparation of 2-(N-methylamino)-3-hydroxymethylpyridine

To a suspension of lithium aluminium hydride (22.0 g 578 mmol) in dry THF (750 ml) in 3 L flask with condenser, dropping funnel, and mechanical stirrer was added dropwise a solution of N-formylamino-nicotinate (37.0 g, 243 mmol) in 400 ml of dry THF. The mixture was stirred for 30 minutes. To the mixture was added dropwise ethyl acetate (80 ml), MeOH (50 ml), DCM (600 ml), and water (60 ml), and then added anhydroud magnesium sulfate (300 g).

After 1 hour stirring, the mixture was filtered and concentrated in vacuo. The residual solution was crystalized with n-hexane to give pure 2-(N-methylamino)-3-hydroxymethylpyridine (19.8 g, Total yield from 2-aminonicotinic acid was 66%).

h) Preparation of [N-methyl-N-3-((tert-butoxycarbonylmethylamino)acetoxymethyl)pyridin-2-yl]carbamic acid 1-chloro-ethyl ester 2-(N-methylamino)-3-hydroxymethylpyridine (22 g, 0.159 mol) and diisopropylamine (36.1 mL, 0.207 mol, 1.3 eq.) were dissolved in dichloromethane(1 L) and cooled in ethanol-ice bath(ca-13° C.). 1-Chloroethyl chloroformate (17.5 mL, 0.161 mol, 1.01 eq.) was added dropwise over a period of 1 h and the mixture was stirred for 1 h. Boc-sarcosine (39.2 g, 0.207 mol, 1.3 eq.) was added to the stirring mixture and WSC (39.7 g, 0.207 mol, 1.3 eq.) was added portionwise over a period of 10 min. To the mixture was added DMAP (5.8 g, 0.047 mol, 0.3 eq.) and the mixture was stirred for 2 h at −7° C. The reaction mixture was concentrated at 25° C. and the residue was dissolved in diethylether (1 L). The solution was transferred to the separate funnel and washed with 0.1N—HCl (500 mL×3), water (500 mL), NaHCO$_3$ aq. (500 mL) and brine (500 mL×2) successively, dried over MgSO$_4$ and concentrated under reduced pressure. The obtained residue (48.2 g, ca 72.9% yield) was used for the next step without purification. $^1$H-NMR (270 MHz, CDCl$_3$): δ 1.42 (9H, d, J=24.1), 1.57 (1.5H, br.s), 1.88 (1.5H, br.s), 2.94 (3H, s), 3.37 (3H, s), 4.00 (2H, d, J=13.5), 5.18 (2H, d, J=21.1), 6.58(1H, q, J=5.45, 11.0), 7.30(1H, s), 7.82(1H, d, J=6.9), 8.47 (1H, s); FAB-MS: m/z 416 (M+H)$^+$.

The following compounds in Example 3.1.-3.25. were obtained according to a manner analogous to those of Example 3.

3.1.

[N-methyl-N-2-[(tert-butoxycarbonylmethylamino)acetoxymethyl]phenyl]carbamic acid chloromethylester. Physical form: colorless oil; LC-MS: m/z 401(M+1)$^+$; $^1$H-NMR (CDCl$_3$): δ1.37 (s, 9/2H), 1.46 (s, 9/2H), 2.93 (s, 3H), 3.29 (s, 3H), 3.93-4.02 (m, 2H), 3.95 (s, 1H), 4.03 (s, 1H), 5.15 (s, 2H), 5.57-5.84 (m, 2H), 7.15-7.49 (m, 4H).

3.2.

[N-methyl-N-2-[(tert-butoxycarbonylmethylamino)acetoxymethyl]phenyl]carbamic acid 1-chloro-ethyl ester. Physical form: colorless oil; LC-MS: m/z 415(M+1)$^+$; $^1$H-NMR (CDCl$_3$): δ1.37 (s, 9/2H), 1.46 (s, 9/2H), 1.55-1.60 (m, 9/4H), 1.90 (d, d=5.6 Hz, 3/4H), 2.93 (s, 3H), 3.29 (s, 3H), 3.94-4.05 (m, 2H), 5.10-5.19 (m, 2H), 6.51-6.63 (m, 1H), 7.11-7.48 (m, 4H).

3.3.

[N-methyl-N-2-[(tert-butoxycarbonylmethylamino)acetoxymethyl]-4,5-difluoro-phenyl]carbamic acid 1-chloro-ethyl ester. Physical form: colorless oil; LC-MS: m/z 451 (M+1)$^+$; $^1$H-NMR (CDCl$_3$): δ1.39 (s, 9/2H), 1.47 (s, 9/2H), 1.59-1.64 (m, 9/4H), 1.89 (d, J=5.3 Hz, 3/4H), 2.94 (s, 3H), 3.26 (s, 3H), 3.96-4.03 (m, 2H), 5.07-5.16 (m, 2H), 6.51-6.61 (m, 1H), 6.96-7.37 (m, 2H).

3.4.

[N-methyl-N-2-[(tert-butoxycarbonylmethylamino)acetoxymethyl]-4-fluoro-phenyl]carbamic acid 1-chloro-ethyl ester. Physical form: light yellow oil; LC-MS: m/z 433 (M+1)$^+$; $^1$H-NMR (CDCl$_3$): δ1.38 (9/2H, s), 1.44 (9/2H, s), 1.55 (3/2H, d, J=5.61 Hz), 1.59 (3/2H, d, J=5.61 Hz), 2.92 (3H, brs), 3.18~3.30 (3H, m), 3.87~4.08 (2H, m), 4.95~5.18 (2H, m), 6.44~6.60 (1H, m), 6.90~7.21 (3H, m).

3.5.

[N-methyl-N-2-[(tert-butoxycarbonylmethylamino)acetoxymethyl]-4,5-dimethoxy-phenyl]carbamic acid chloromethyl ester. Physical form: colorless oil; LC-MS: m/z 461 (M+1)$^+$; $^1$H-NMR(CDCl$_3$): δ1.35-1.45(9H, m), 2.92(3H, s), 3.27(3H, s), 3.80-4.00(2H, m), 3.86 (3H, s), 3.90(3H, s), 5.05(2H, m), 5.62-5.84(2H, m), 6.62(1H, br.s), 6.93(1H, br.s).

3.6.

[N-methyl-N-2-[(tert-butoxycarbonylmethylamino)acetoxymethyl]-5-fluoro-phenyl]carbamic acid 1-chloro-ethyl ester. Physical form: colorless oil; LC-MS: m/z 433 (M+1)$^+$; $^1$H-NMR(CDCl$_3$): δ1.37 (s, 9/2H), 1.46 (s, 9/2H), 1.56-1.62 (m, 9/4H), 1.89 (d, J=5.3 Hz, 3/4H), 2.92 (s, 3H), 3.28 (s, 3H), 3.93-4.02 (m, 2H), 5.05-5.13 (m, 2H), 6.52-6.60 (m, 1H), 6.83-7.09 (m, 2H), 7.41-7.49 (m, 1H).

3.7.

[N-methyl-N-2-[(tert-butoxycarbonylmethylamino)acetoxymethyl]-6-methyl-phenyl]carbamic acid 1-chloro-ethyl ester. Physical form: colorless oil; LC-MS: m/z 429 (M+1)$^+$; $^1$H-NMR(CDCl$_3$): 1.36-1.49(9H, m), 1.61(3H, s), 2.18-2.25 (3H, m), 2.92(3H, s), 3.21(3H, s), 3.91-4.05(2H, m), 5.04-5.22(2H, m), 6.51-6.64(1H, m).

3.8.

[N-methyl-N-2-[(tert-butoxycarbonylmethylamino)acetoxymethyl]-4-chloro-phenyl]carbamic acid 1-chloro-ethyl ester. Physical form: colorless oil; LC-MS: m/z 449 (M+1)$^+$; $^1$H-NMR(CDCl$_3$): δ 1.38-1.47(9H, m), 1.59(3H, s), 2.94(3H, s), 3.27(3H, s), 3.94-4.08(2H, m), 5.05-5.17(2H, m), 6.55 (1H, m), 7.02-7.21(1H, m), 7.36(1H, m), 7.45(1H, s).

3.9.

[N-(tert-butoxycarbonylmethylamino)acetoxyethyl-N-2,4-difluoro-phenyl]carbamic acid 1-chloro-ethyl ester. Physical form: colorless oil; LC-MS: m/z 451 (M+1)$^+$; $^1$H-NMR (CDCl$_3$): δ 1.41 (s, 9/2H), 1.46 (s, 9/2H), 1.59-1.64 (m, 9/4H), 1.89 (d, d=5.6 Hz, 3/4H), 2.89 (s, 3H), 3.85-4.00 (m, 4H), 4.27-4.36 (m, 2H), 6.49-6.83 (m, 3H), 7.19-7.32 (m, 1H).

3.10.

[N-methyl-N-2-[(tert-butoxycarbonylmethylamino)acetoxymethyl]-5-chloro-phenyl]carbamic acid 1-chloro-ethyl ester. Physical form: colorless oil; LC-MS: m/z 449 (M+1)$^+$; $^1$H-NMR (270 MHz, CDCl$_3$): δ 1.37 (4.5H, s), 1.46 (4.5H, s), 1.59 (2H, br.s), 1.89 (1H, br.s), 2.92 (3H, s), 3.28 (3H, s), 3.94 (1H, s), 4.02 (1H, s), 5.06 (1H, br.s), 5.10 (1H, br.s), 6.39-6.59 (1H, m), 7.17-7.23 (1H, m), 7.31-7.43 (2H, m)

3.11.

[N-methyl-N-2-[(tert-butoxycarbonylmethylamino)acetoxymethyl]-5-nitro-phenyl]carbamic acid 1-chloro-ethyl ester. Physical form: yellow oil; LC-MS: 460(M+1)$^+$; $^1$H-NMR (CDCl$_3$): δ1.22~1.70(11H, m), 1.88(1H, d, J=4.95 Hz), 2.90(3H, br.s), 3.29(3H, br.s), 3.90~4.08 (2H, m), 5.03~5.28(2H, m), 6.46~6.61 (1H, m), 7.55~7.72(1H, m), 7.96~8.27(2H, m).

3.12.

5(S)-[(tert-butoxycarbonyl)methylaminoacethoxymethyl]-1-[chloromethyloxycarbonyl]-2-pyrrolidone. Physical form: colorless oil; LC-MS: m/z 379 (M+1)$^+$; $^1$H-NMR (CDCl$_3$): δ 1.43(9H, m), 1.92-2.80(4H, m), 2.90(3H, br.s), 3.88-4.56(5H, m), 5.79-5.90(2H, m).

3.13.

[N-methyl-N-2-[(tert-butoxycarbonylmethylamino)acetoxymethyl]-3-fluoro-phenyl]carbamic acid 1-chloro-ethyl ester. Physical form: colorless oil; LC-MS: m/z 433 (M+1)$^+$; $^1$H-NMR (CDCl$_3$): δ 1.38 (s, 9/2H), 1.44 (s, 9/2H), 1.58-1.62 (m, 9/4H), 1.89 (d, J=5.6 Hz, 3/4H), 2.91 (s, 3H), 3.28 (s, 3H), 3.90-3.98 (m, 2H), 5.00-5.35 (m, 2H), 6.50-6.61 (m, 1H), 6.96-7.14 (m, 2H), 7.31-7.42 (m, 1H).

3.14.

[N-methyl-N-2-[(tert-butoxycarbonylmethylamino)acetoxymethyl]-5-cyano-phenyl]carbamic acid 1-chloro-ethyl ester. Physical form: colorless oil; LC-MS: m/z 440 (M+1)$^+$; $^1$H-NMR(CDCl$_3$): δ 1.36-1.48(9H, m), 1.57(3H, s), 2.93(3H, d, J=4.9 Hz), 3.29(3H, s), 3.88-4.04(2H, m), 5.06-5.20(2H, m), 6.53(1H, m), 6.81-6.95(1H, m), 7.46-7.68(2H, m).

3.15.

[N-methyl-N-2-[(tert-butoxycarbonylmethylamino)acetoxymethyl]-3-chloro-phenyl]carbamic acid 1-chloro-ethyl ester. Physical form: colorless oil; LC-MS: m/z 449 (M+1)$^+$; $^1$H-NMR(CDCl$_3$): δ 1.39 (s, 9/2H), 1.44 (s, 9/2H), 1.57-1.61 (m, 9/4H), 1.89 (m, 3/4H), 2.91 (s, 3H), 3.26 (s, 3H), 3.93-4.03 (m, 2H), 5.06-5.39 (m, 2H), 6.50-6.56 (m, 1H), 7.07-7.45 (m, 3H).

3.16.

[N-methyl-N-2-[(tert-butoxycarbonylmethylamino)acetoxymethyl]-4-cyano-phenyl]carbamic acid 1-chloro-ethyl ester. Physical form: colorless oil; LC-MS: m/z 440 (M+1)$^+$.

3.17.

[N-methyl-N-2-[(tert-butoxycarbonylmethylamino)acetoxymethyl]-5-trifluoromethyl-phenyl]carbamic acid 1-chloro-ethyl ester. Physical form: colorless oil; LC-MS: m/z 483 (M+1)$^+$; $^1$H-NMR(CDCl$_3$): δ 1.36-1.45(9H, m), 1.56 (3H, s), 2.93(3H, s), 3.31(3H, s), 3.95-4.08(2H, m), 5.12-5.21 (2H, m), 6.56(1H, m), 7.37-7.60(3H, m).

3.18.

[N-methyl-N-2-[(tert-butoxycarbonylamino)acetoxymethyl]-3-chloro-phenyl]carbamic acid 1-chloro-ethyl ester. Physical form: colorless oil; LC-MS: m/z 449 (M+1)$^+$; $^1$H-NMR(CDCl$_3$): δ 1.44 (s, 9H), 1.57-1.61 (m, 2H), 1.85-1.89 (m, 1H), 3.24 (s, 1H), 3.26 (s, 2H), 3.88-3.94 (m, 2H), 5.03 (bs, 1H), 5.13-5.36 (m, 2H), 6.48-6.56 (m, 1H), 7.08-7.45 (m, 3H).

3.19.

[N-ethyl-N-2-[(tert-butoxycarbonylmethylamino)acetoxymethyl]-3-chloro-phenyl]carbamic acid 1-chloro-ethyl ester. Physical form: colorless oil; LC-MS: m/z 463 (M+1)$^+$; $^1$H-NMR(CDCl$_3$): δ 1.14-1.21 (m, 3H), 1.41 (s, 9/2H), 1.44 (s, 9/2H), 1.56-1.66 (m, 9/4H), 1.89 (m, 3/4H), 2.91 (s, 3H), 3.39-3.52 (m, 1H), 3.80-4.05 (m, 3H), 5.03-5.14 (m, 1H), 5.26-5.40 (m, 1H), 6.49-6.60 (m, 1H), 7.04-7.46 (m, 3H).

3.20.

[N-methyl-N-3-[(tert-butoxycarbonylamino)acetoxymethyl]pyridin-2-yl]carbamic acid 1-chloro-ethyl ester. Physical form: colorless oil; LC-MS: m/z 401 (M)$^+$; $^1$H-NMR (270 MHz, CDCl$_3$): δ 1.43 (9H, s), 1.55 (3/2H, br.s), 1.87 (3/2H, br.s), 3.20 (3H, s), 3.93 (1H, s), 3.96 (1H, s), 5.15 (1H, br.s), 5.20 (1H, br.s), 5.64 (1H, br.s), 6.57 (1H, m), 7.32 (1H, m), 7.85 (1H, m), 8.46 (1H, m)

3.21.

[N-methyl-N-2-[(tert-butoxycarbonylmethylamino)acetoxymethyl]-3-methyl-phenyl]carbamic acid 1-chloro-ethyl ester. Physical form: colorless oil; LC-MS: m/z 429(M+1)$^+$.

3.22.

[N-ethoxycarbonyl-N-2-((tert-butoxycarbonylmethylamino)acetoxymethyl)pheny]carbamic acid 1-chloro-ethyl ester. Physical form: colorless oil; LC-MS: m/z 473(M+1)$^+$; $^1$H-NMR (CDCl$_3$): δ 1.24(3H, t, J=6.9 Hz) 1.41-1.47(9H, m), 1.66(3H, d, J=5.6 Hz), 2.91(3H, d, J=3.6 Hz), 3.92-4.00(2H, m), 4.26(2H, q, J=6.9 Hz), 5.13(2H, m), 6.53(1H, q, J=5.6 Hz), 7.12-7.21(1H, m), 7.38-7.50(3H, m).

3.23.

[N-pivaloyl-N-2-((tert-butoxycarbonylmethylamino)acetoxymethyl)phenyl]carbamic acid 1-chloro-ethyl ester. Physical form: colorless oil; LC-MS: m/z 485(M+1)$^+$; $^1$H-NMR (CDCl$_3$): δ 1.33-1.49(18H, m), 1.65(3H, d, J=5.6 Hz), 2.91(3H, d, J=4.0 Hz), 3.91-4.05(2H, m), 5.03-5.26(2H, m), 6.50(1H, q, J=5.6 Hz), 7.06-7.19(1H, m), 7.36-7.53(3H, m).

3.24.

[N-pivaloyl-N-2-(tert-butoxycarbonylmethylaminoacetoxy)ethyl]carbamic acid 1-chloro-ethyl ester. Physical form: colorless oil; LC-MS: m/z 423(M+1)$^+$; $^1$H-NMR (CDCl$_3$): δ 1.33(9H, s), 1.36-1.49(9H, m), 1.87(3H, d, J=5.9 Hz), 2.91 (3H, s), 3.84-3.96(4H, m), 4.28(2H, t, J=5.3 Hz), 6.56(1H, q, J=5.9 Hz).

3.25.

[N-ethoxycarbonyl-N-2-(tert-butoxycarbonylmethylaminoacetoxy)ethyl]carbamic acid 1-chloro-ethyl ester. Physical form: colorless oil; LC-MS: m/z 411 (M+1)$^+$; $^1$H-NMR (CDCl$_3$): 1.35(3H, t, J=6.9 Hz), 1.41-1.49(9H, m), 1.86(3H, d, J=5.6 Hz), 2.92(3H, s), 3.88-4.06(4H, m), 4.29-4.38(4H, m), 6.57(1H, q, J=5.6 Hz).

Example 4

[N-ethyl-N-(tert-butoxycarbonylethylamino)ethyl]carbamic acid 1-chloro-ethyl ester a) Preparation of Ethyl-(2-ethylamino-ethyl)-carbamic acid tert-butyl ester To a solution of N,N'-diethylethylene diamine(r) (5 g, 43.0 mmol) in tetrahydrofuran (20 ml) was added di-tert-butyl dicarbonate (3.30 ml, 14.3 mmol) in tetrahydrofuran (20 ml) dropwise at 0° C. The reaction temperature was gradually up to room temp. After stirring overnight, the solvent was removed in vacuo. The residue was purified by column chromatography (50% methenol-dichloromethane and 0.5% triethylamine) to afford ethyl-(2-ethylamino-ethyl)-carbamic acid tert-butyl ester (3.5 g) as light yellow oil.

b) Preparation of [N-ethyl-N-(tert-butoxycarbonylethylamino)ethyl]carbamic acid-1-chloro-ethyl ester To a solution of ethyl-(2-ethylamino-ethyl)-carbamic acid tert-butyl ester (1 g, 4.62 mmol) and N,N-diisopropylethylamine (1.05 ml, 6.01 mmol) in dichloromethane (25 ml) was added chloroethylchloroformate (0.6 ml, 5.54 mmol) at 0° C. The reaction temperature was warm up to room temperature. After stirring overnight, the reaction mixture was quenched with water and extracted with dichloromethane. The combined organic phase was washed with water and brine, dried over anhydrous magnesium sulfate, filtered and concentrated in vacuo. The crude product was purified by column chromatography (30% ethyl acetate-hexane) to afford [N-ethyl-N-(tert-butoxycarbonyl ethylamino)ethyl]carbamic acid 1-chloro-ethyl ester (t) as light yellow oil (1.14 g, 3.52 mmol, 76%). Physical form: light yellow oil; EI-MS: m/z 322(M$^+$); $^1$H-NMR (CDCl$_3$): δ 1.00~1.18(6H, m), 1.42(9H, s), 1.77 (3H, d, J=5.9 Hz), 3.10~3.49(8H, m), 6.49~6.64(1H, m).

The following compounds in Example 4.1.-4.5. were obtained according to a manner analogous to those of Example 4.

4.1.

[N-methyl-N-2-(tert-butoxycarbonyl methylamino)ethyl]carbamic acid 1-chloro-ethyl ester. Physical form: colorless oil; LC-MS: 295(M+1)$^+$; $^1$H-NMR (CDCl$_3$): δ 1.40 (9H, s), 1.73~1.83 (3H, m), 2.85 (3H, s), 2.92 (3H, d, J=5.28 Hz), 3.18~3.54 (4H, m), 6.46~6.61 (1H, m).

4.2.

[N-methyl-N-3-(tert-butoxycarbonyl methylamino)propyl]carbamic acid 1-chloro-ethyl ester. Physical form: colorless oil; LC-MS: m/z 309 (M+1)$^+$; $^1$H-NMR (CDCl$_3$): δ 1.43 (9H, s), 1.78 (3H, d, J=5.61 Hz), 2.83 (3H, brs), 2.90 (3H, d, J=6.27 Hz), 3.11~3.38(6H, m), 6.48~6.62(1H, m).

4.3.

3(S)-[tert-butoxycarbonylamino]-1-[1-chloroethyloxycarbonyl]pyrrolidine. Physical form: white amorphous; LC-MS: m/z 293(M+1)$^+$; $^1$H-NMR(CDCl$_3$): δ 1.43(9H, s), 1.77-2.23(5H, m), 3.20-3.75(4H, m), 4.20(1H, m), 4.60(1H, m), 6.58(1H, m).

4.4.

2(S)-[tert-butoxycarbonylaminomethyl]-1-[1-chloroethyloxycarbonyl]pyrrolidine. Physical form: colorless oil; LC-MS: m/z 307(M+1)$^+$; $^1$H-NMR (CDCl$_3$): δ 1.47(9H, s), 1.65-2.05(7H, m), 3.20-3.45(4H, m), 3.95(1H, m), 6.56(1H, m).

4.5.

[N-methyl-N-2-(tert-butoxycarbonylmethylamino)-1,2-trans-cyclohexan-1-yl]carbamic acid 1-chloro-ethyl ester. Physical form: light brown oil; LC-MS: m/z 349 (M+1)$^+$.

Example 5

[[N-methyl-N-2-(acetoxymethyl)phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride a) Preparation of [[N-methyl-N-2-(acetoxymethyl)phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride A solution of 1-[3-[4-(4-cyano-phenyl)-thiazol-2-yl]-2-(2,5-difluoro-phenyl)-2-hydroxy-butyl-1H-[1,2,4]triazol (200 mg, 0.457 mmol), sodium iodide (6.8 mg 0.045 mmol) and acetic acid 2-(chloromethoxycarbonyl-methyl-amino)-benzyl ester 150 mg, 0.552 mmol) was stirred for 6 h at ambient temperature and then at 80° C. for 3 h under Ar atmosphere. The reaction mixture was concentrated under reduced pressure and the resulting material was eluted on a column of silica gel (Kusano Si-5, eluent dichloromethane:methanol=20:1). The fractions containing the product were concentrated under reduced pressure giving the title compound a) as colorless amorphous (204.5 mg, 63%). $^1$H-NMR (270 MHz, DMSO-d$_6$): δ 1.20 (3H, d, J=6.9), 1.99 (3H, s), 3.12 (2.4H, s), 3.15 (0.6H, s), 4.15 (1H, q, J=7.3), 4.79-4.91 (3H, m), 5.09 (1H, d, J=14.8), 5.76 (1H, s), 5.90-6.10 (1.6H, m), 6.17 (0.4H, br.s), 6.61-6.66 (1H, m), 7.05-7.15 (1H, m), 7.26-7.44 (6H, m), 7.91-7.96 (2H, m), 8.20-8.24 (2H, m), 8.49 (1H, s), 9.01 (0.8H, br.d, J=3.6), 9.12 (0.2H, br.s), 10.16 (0.8H, br.d, J=4.9), 10.27 (0.2H, br.s); FAB-MS: 673 (M-Cl)$^+$; Ratio of Retention Time in HPLC: 1.79 (see Example D).

The following compounds in Example 5.1.-5.7. were obtained according to a manner analogous to those of Example 5.

5.1.

[[N-methyl-N-phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride. Physical form: colorless amorphous powder; FAB-MS: 601 (M-Cl)$^+$; Ratio of Retention Time in HPLC: 1.10 (see Example D).

5.2.

1-[[N-methyl-N-3-(acetoxymethyl)pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: 688 (M-Cl)$^+$; Ratio of Retention Time in HPLC: 0.82 (see Example D). $^1$H-NMR (DMSO-d$_6$): δ 1.20(3H, d, J=7.3 Hz), 1.50-1.88(3H, m), 2.02 (3H, m), 3.18(3H, br.s), 4.16(1H, m), 4.70-5.12(4H, m), 6.80 (1H, m), 7.05-7.48(4H, m), 7.91(3H, br.d, J=8.3 Hz), 8.21 (2H, d, J=8.3 Hz), 8.46(2H, br.s), 9.21(1H, m), 10.4(1H, m).

5.3.

1-[(N-acetyl-N-methyl)carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide. Physical form: pale yellow solid; LC-MS: m/z 581 (M-l)$^+$; Ratio of Retention Time in HPLC: 0.77 (see Example D).

5.4.

[[2(S)-(acetoxymethyl)pyrrolidin-1-yl]carbonyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide. Physical form: colorless amorphous powder; FAB-MS: 637 (M-l)$^+$; Ratio of Retention Time in HPLC: 1.36 (see Example D); $^1$H-NMR(CDCl$_3$): δ 1.26(3H, d, J=6.6 Hz), 1.82-2.15(7H, m), 3.30-4.40(6H, m), 4.90-5.15(2H, m), 6.15-7.30(5H, m), 7.66(1H, s), 7.80(2H, d, J=8.5 Hz), 8.11 (2H, d, J=8.5 Hz), 8.50(1H, br.s), 11.3(1H, br.s).

5.5.

[[N-methyl-N-2-(acetoxy)ethyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide. Physical form: colorless amorphous powder; FAB-MS: 611 (M-l)$^+$; Ratio of Retention Time in HPLC: 0.78 (see Example D). $^1$H-NMR (CDCl$_3$): δ 1.26(3H, d, J=7.0 Hz), 2.02(3H, s), 2.98(3H, br.s), 3.50(2H, m), 4.10-4.32 (3H, m), 4.88-5.15(2H, m), 6.22-6.40(2H, m), 6.95-7.22(3H, m), 7.66 (1H, s), 7.80(2H, d, J=8.2 Hz), 8.11 (2H, d, J=8.2 Hz), 8.51 (1H, br.s), 11.2(1H, m).

5.6.

[[N-methyl-N-3-(acetoxy)propyl)]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide. Physical form: white powder; LC-MS: m/z 625 (M-l)$^+$; Ratio of Retention Time in HPLC: 0.83 (see Example D).

5.7.

[[N-2-(methyl)phenyl-N-2-(acetoxy)ethyl]carbamoyloxy]methyl-1-[(2R,3R)-2-(2,5-difluoro phenyl)-2-hydroxy-3-[4-(4-cyanophenyl)thiazol-2-yl]butyl]-1H-[1,2,4]triazol-4-ium iodide. Physical form: colorless amorphous powder; FAB-MS: 687 (M-l)$^+$; Ratio of Retention Time in HPLC:1.79 (see Example D).

Example 6

1-[[N-methyl-N-2-(isopropylaminomethyl)phenyl] carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride a) Preparation of 1-[[N-methyl-N-2-(t-butoxycarbonyl-isopropylaminomethyl)phenyl]carbamoyloxy]ethyl-1-[(2R,3R)-2-(2,5-difluorophenyl)-2-hydroxy-3-4-(4-cyanophenyl)thiazol-2-yl]butyl]-1H-[1,2,4]triazol-4-ium chloride To a solution of [N-methyl-N-2-((tert-butoxycarbonyliso-propylamino)methyl)phenyl]carbamic acid 1-chloro-ethyl ester (143 mg, 0.342 mmol) in acetonitrile (1 ml) was added the azole compound (163 mg, 0.372 mmol) and catalytic amount of sodium iodide at 70° C. After stirring overnight, the solvent was removed and extracted with ethyl acetate. The organic phase was washed with water and brine. The solvent was removed in vacuo. The residue was purified by column chromatography (ethyl acetate to 10% methanel-dichloromethane) to afford 1-[[N-methyl-N-2-(t-butoxycarbonyl-isopropylaminomethyl)phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride (155 mg, 0.189 mmol, 51%) as off-white amorphous.

b) Preparation of 1-[[N-methyl-N-2-(isopropylaminomethyl)phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride To a solution (1 ml) of 1-[[N-methyl-N-2-(t-butoxycarbo-nylisopropylamino-methyl)phenyl]carbamoyloxy]ethyl-1-[(2R,3R)-2-(2,5-difluorophenyl)-2-hydroxy-3-[4-(4-cyano-phenyl)thiazol-2-yl]butyl]-1H-[1,2,4]triazol-4-ium chloride (148 mg, 0.180 mmol) in ethyl acetate (1 ml) was added 4N hydrogen chloride ethyl acetate solution (1 ml) at room temperature. After stirring for 2 hours, the precipitate was filtered and washed with ethyl acetate. The precipitate was dried up to afford 1-[[N-methyl-N-2-(isopropylamino-methyl)phenyl]carbamoyloxy]ethyl-1-[(2R,3R)-2-(2,5-difluorophenyl)-2-hydroxy-3-[4(4-cyanophenyl)thiazol-2-yl]butyl]-1H[1,2,4]triazol-4-ium chloride hydrochloride (137 mg, 0.180 mmol, quant) as off-white amorphous. Physical form: off-white amorphous powder; FAB-MS: 686 (M-HCl-Cl)$^+$; $^1$H-NMR (DMSO): δ 1.10~1.64 (12H, m), 3.10~3.30 (3H, m), 3.79~4.28 (2H, m), 4.56~5.22 (5H, m), 6.59~6.84 (1H, m), 7.02~7.49 (6H, m), 7.99 (2H, d, J=8.25 Hz), 8.20 (2H, d, J=7.92 Hz), 8.48 (1H, s), 9.08~9.39 (3H, m), 10.35~10.62 (1H, m).

The following compounds in Example 6.1.-6.3. were obtained according to a manner analogous to those of Example 6.

6.1.

1-[[N-2-[(isopropylamino)methyl]phenyl]carbamoyloxy] ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: 672 (M-HCl-Cl)$^+$. $^1$H-NMR (DMSO): δ 1.09~1.39 (6H, m), 1.82 (3H, brs), 3.30 (1H, brs), 3.98~4.20 (3H, m), 4.78 (1H, dd, J=4.95, 9.51 Hz), 5.08 (2H, d, J=14.18 Hz), 6.73~6.92 (1H, m), 7.05~7.48 (7H, m), 7.58~7.68 (1H, m), 7.92 (2H, d, J=7.92 Hz), 8.22 (2H, d, J=8.25 Hz), 8.49 (1H, d, J=2.97 Hz), 9.17~9.37 (3H, m), 9.96 (1H, brs), 10.50 (1H, d, J=13.86 Hz).

6.2.

1-[[N-2-[(pentan-3-ylamino)methyl]phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: 700 (M-HCl-Cl)$^+$. $^1$H-NMR (DMSO): δ 0.78~0.97 (6H, m), 1.07~1.28 (3H, m), 1.59~1.90 (4H, m), 2.96 (1H, brs), 4.08~4.19 (3H, m), 4.79 (1H, dd, J=5.28, 9.51 Hz), 5.08 (2H, d, J=14.18 Hz), 6.74~6.99 (2H, m), 7.08~7.46 (6H, m), 7.92 (1H, dd, J=1.32, 3.25 Hz), 8.19 (2H, d, J=8.58 Hz), 8.48 (2H, d, J=2.97 Hz), 9.21 (1H, brs), 9.30 (1H, s), 10.00 (1H, brs), 10.54 (1H, d, J=16.82 Hz).

6.3.

1-[[N-2-[(methylamino)methyl]phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: 658 (M-HCl-Cl)$^+$. $^1$H-NMR (DMSO): δ 1.13~1.32 (4H, m), 1.48~1.65 (2H, m), 1.78~1.96 (1H, m), 3.08~3.32 (4H, m), 3.80~4.25 (3H, m), 4.70~4.89 (1H, m), 5.06 (1H, d, J=13.85 Hz), 6.38 (1H, brs), 6.58~6.84 (1H, m), 7.05~7.52 (7H, m), 7.72~8.15 (1H, m), 7.94 (2H, d, J=8.24 Hz), 8.22 (2H, d, J=8.25 Hz), 8.49 (1H, s), 9.08~9.42 (1H, m), 9.78 (1H, brs), 10.30~10.77 (1H, m).

Example 7

1-[[N-methyl-N-3-[(methylamino)acetoxymethyl] pyridin-2-yl]carbamoyloxy]ethyl-1-[(2R,3R)-2-(2,5-difluorophenyl)-2-hydroxy-3-[4-(4-cyanophenyl) thiazol-2-yl]butyl]-1H-[1,2,4]triazol-4-ium chloride hydrochloride a) Preparation of 1-[[N-methyl-N-3-[(t-butoxycarbo-nylmethylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride

[N-methyl-N-3-((tert-butoxycarbonylmethylamino)ac-etoxymethyl)pyridin-2-yl]carbamic acid 1-chloro-ethyl ester (q) (55 g, 0.132 mol, 1.4 eq) and the azole compound of Example 5a) (41.2 g, 0.0944 mol) was dissolved in CH$_3$CN (350 mL) and warmed to 45-50° C. To the solution was added NaI (19.7 g, 0.131 mol, 1.4 eq) and stirred for 15 h. After cooling to room temperature, the reaction mixture was concentrated under reduced pressure. The obtained residue was purified by silicagel column chromatography ((eluent: from AcOEt to AcOEt/MeOH (10/1, v/v) gradient) to give the product as its iodide form (78.7 g, 88.4% yield).

The iodide (66.5 g, 0.07 mol) was dissolved in MeOH (300 mL) and distilled water (200 mL) at 0° C. and strong anion exchange resin[Dia Ion SA10A (200 g)] was added to the solution. The mixture was stirred using an evaporator. After 1 h, the mixture was filtered, washed with methanol and the filtrate was evaporated. The obtained residue was diluted with water (200 mL), brine (200 mL) and ethyl acetate (500 mL). The organic layer was extracted with ethyl acetate and combined ethyl acetate layer was dried over Na$_2$SO$_4$ and concentrated under reduced pressure. The obtained residue was purified by silicagel column chromatography ((eluent:DCM/MeOH(10/1, v/v)) to give the product (52.1 g, 86.7% yield).

b) Preparation of 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyano-phenyl)thiazol-2-yl]butyl]-1H-[1,2,4]triazol-4-ium chloride hydrochloride 1-[[N-methyl-N-3-[(t-butoxycarbonylmethylamino)acetoxymethyl]pyridin-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride (51.5 g, 0.06 mol) was dissolved in dry ethyl acetate (900 mL) and cooled to 0° C. To this solution 4N—HCl/EtOAc (0.8 mol, 200 mL) was added dropwise. The mixture was stirred vigorously for 4 h at room temperature. After filtration, the filtrate was washed with EtOAc under $N_2$. The obtained white solid was dried through $N_2$ for 2 d, further dried at 70° C. under reduced pressure for 24 h. The dried solid was dissolved in distilled water (2 L) and washed with dichloromethane (2 L×5) and hexane (1 L×2) and water layer was freezed dried to give the final product (32.8 g). $^1$H-NMR (400 MHz, 100° C., DMSO-$d_6$): δ 1.25 (3H, d, J=6.1), 1.72 (3H, br.s), 2.58 (3H, d, J=4.0), 3.21 (3H, s), 3.94 (2H, d, J=2.8), 4.16 (1H, q, J=6.1), 4.85-4.90 (1H, m), 5.08-5.14 (1H+2H, m), 6.84 (1H, q, J=6.0), 7.14-7.17 (2H, m), 7.18-7.27 (1H, m), 7.41-7.45 (1H, m), 7.86 (2H, d, J=8.4), 8.00 (1H, d, J=6.8), 8.16 (2H, d, J=8.4), 8.28 (1H, s), 8.44-8.48 (1H, m), 9.17 (1H, s), 10.47(1H, d, J=18.0); FAB-MS: m/z 717 (M-2HCl-Cl)$^+$:

The following compounds in Example 7.1.-7.25. were obtained according to a manner analogous to those of Example 7.

7.1.
[[N-methyl-N-2-[(methylamino)acetoxymethyl]phenyl]carbamoyloxy]methyl-[(2R,3R)-2-(2,5-difluorophenyl)-2-hydroxy-3-[4-(4-cyanophenyl)thiazol-2-yl]butyl]-[1,2,4]triazol-4-ium chloride hydrochloride. Physical form: colorless amorphous powder; FAB-MS: m/z 702 (M-HCl-Cl)$^+$; Ratio of Retention Time in HPLC: 0.78 (see Example D).

7.2.
1-[[N-methyl-N-2-[(methylamino)acetoxymethyl]phenyl]carbamoyloxy]ethyl-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 716 (M-HCl-Cl)$^+$; Ratio of Retention Time in HPLC: 0.75 (see Example D).

7.3.
1-[[N-methyl-N-2-(methylamino)acetoxymethyl-4,5-difluorophenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 752 (M-HCl-Cl)$^+$; Ratio of Retention Time in HPLC: 0.94 (see Example D).

7.4.
1-[[N-methyl-N-2-(methylamino)acetoxymethyl-4-fluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: colorless amorphous powder; FAB-MS: m/z 734 (M-HCl-Cl)$^+$; Ratio of Retention Time in HPLC: 0.83 (see Example D). $^1$H-NMR (DMSO): δ 1.15~1.30 (3H, m), 1.49~1.61 (3H, m), 1.79~1.89 (1H, m), 2.52~2.65 (3H, m), 3.05~3.21 (4H, m), 3.98~4.22 (2H, m), 3.67~5.25 (5H, m), 6.66~6.93 (1H, m), 7.03~7.53 (4H, m), 7.95 (2H, d, J=8.24 Hz), 8.21 (2H, d, J=8.25 Hz), 8.48 (1H, brs), 9.06~9.30 (1H, m), 9.32~9.62 (2H, m), 10.32~10.53 (1H, m).

7.5.
[[N-methyl-N-2-(methylamino)acetoxymethyl-4,5-dimethoxy-phenyl]carbamoyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: colorless amorphous powder; FAB-MS: m/z 762 (M-HCl-Cl)$^+$; Ratio of Retention Time in HPLC: 0.79 (see Example D). $^1$H-NMR(DMSO-$d_6$): δ 1.18(3H, d, J=7.3 Hz), 2.50(3H, br.s), 3.12(3H, br.s), 3.65-4.18(11H, m), 4.79-5.12(2H, m), 5.90-7.38(7H, m), 7.92(2H, br.d, J=8.2 Hz), 8.21 (2H, br.d, J=8.2 Hz), 8.50(1H, br.s), 9.05(1H, br.s), 9.45 (2H, br.s), 10.2(1H, br.s).

7.6.
1-[[N-methyl-N-2-(methylamino)acetoxymethyl-5-fluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 734 (M-HCl-Cl)$^+$; Ratio of Retention Time in HPLC: 0.80 (see Example D).

7.7.
1-[[N-methyl-N-2-(methylamino)acetoxymethyl-6-methyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: pale yellow solid. LC-MS: m/z 731 (M+H)$^+$. Ratio of Retention Time in HPLC: 0.70 (see Example D).

7.8.
1-[[N-methyl-N-2-(methylamino)acetoxymethyl-4-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: pale yellow solid. LC-MS: m/z 750 (M-HCl-I)$^+$; Ratio of Retention Time in HPLC: 0.70 (see Example D).

7.9.
1-[[N-(methylamino)acetoxyethyl-N-2,4-difluorophenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 752 (M-HCl-Cl)$^+$; Ratio of Retention Time in HPLC: 0.76 (see Example D).

7.10.
1-[[N-methyl-N-2-(methylamino)acetoxymethyl-5-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: colorless amorphous powder; FAB-MS: m/z 750 (M-HCl-I)$^+$; Ratio of Retention Time in HPLC: 0.60 (see Example D).

7.11.
1-[[N-methyl-N-2-(methylamino)acetoxymethyl-5-nitrophenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 761 (M-HCl-Cl)$^+$; Ratio of Retention Time in HPLC: 0.83 (see Example D). $^1$H-NMR (DMSO): δ 1.10~1.31 (4H, m), 1.45~1.65 (2H, m), 1.79~1.96 (2H, m), 3.08~3.30 (4H, m), 3.95~4.25 (4H, m), 4.65~4.90 (1H, m), 4.99~5.25 (1H, m), 6.63~6.89 (1H, m), 7.05~7.46 (4H, m), 7.78~8.04 (4H, m), 8.12~8.39 (4H, m), 8.50 (1H, s), 9.02~9.38 (1H, m), 9.60 (1H, brs), 10.31~10.69 (1H, m).

7.12.

[[5(S)-(methylamino)acethoxymethyl-2-pyrrolidon-1-yl]carbonyloxy]methyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: colorless amorphous powder; FAB-MS: m/z 680 (M-HCl-I)$^+$; Ratio of Retention Time in HPLC: 0.87 (see Example D). $^1$H-NMR (DMSO-d$_6$): δ 1.19(3H, d, J=7.3 Hz), 1.83-2.76 (7H, m), 3.90-4.42(6H, m), 4.81(1H, br.d, J=14.5 Hz), 5.10 (1H, br.d, J=14.5 Hz), 6.25(2H, m), 7.05-7.38(3H, m), 7.93 (2H, br.d, J=8.3 Hz), 8.21 (2H, br.d, J=8.3 Hz), 8.46(1H, br.s), 9.11 (1H, br.s), 9.20(2H, br.s), 10.2(1H, br.s).

7.13.

1-[[N-methyl-N-2-(methylamino)acetoxymethyl-3-fluoro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 734 (M-HCl-Cl)$^+$; Ratio of Retention Time in HPLC: 0.77 (see Example D).

7.14.

1-[[N-methyl-N-2-(methylamino)acetoxymethyl-5-cyano-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: pale yellow powder. LC-MS: m/z 741 (M-HCl-Cl)$^+$; Ratio of Retention Time in HPLC: 0.50 (see Example D).

7.15.

1-[[N-methyl-N-2-(methylamino)acetoxymethyl-3-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 750 (M-HCl-Cl)$^+$; Ratio of Retention Time in HPLC: 0.88 (see Example D).

7.16.

1-[[N-methyl-N-2-(methylamino)acetoxymethyl-4-cyano-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 741 (M-HCl-Cl)$^+$; Ratio of Retention Time in HPLC: 0.82 (see Example D). $^1$H-NMR (CD$_3$OD): δ 1.22-2.00(6H, m), 2.73-2.77(6H, m), 3.23-3.34(1H, m), 3.88-4.10(3H, m), 4.28-4.40(1H, m), 5.06-5.24(2H, m), 5.29-5.33(1H, m), 7.00-7.30 (3H, m), 7.40-7.56(1H, m), 7.73-7.85(3H, m), 7.86-7.95(1H, m), 8.10-8.22(4H, m), 8.80-9.05(1H, m).

7.17.

1-[[N-methyl-N-2-(methylamino)acetoxymethyl-5-trifluoromethyl-phenyl]carbamoy-loxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: pale yellow powder. LC-MS: m/z 784 (M-HCl-I)$^+$; Ratio of Retention Time in HPLC: 1.09 (see Example D).

7.18.

1-[[N-methyl-N-2-(amino)acetoxymethyl-3-chloro-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 736 (M-HCl-Cl)$^+$; Ratio of Retention Time in HPLC: 0.83 (see Example D).

7.19.

1-[[N-ethyl-N-2-(methylamino)acetoxymethyl-3-chlorophenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 764 (M-HCl-Cl)$^+$; Ratio of Retention Time in HPLC: 0.91 (see Example D).

7.20.

1-[[N-methyl-N-3-[(amino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 703 (M-HCl-Cl)$^+$; Ratio of Retention Time in HPLC: 0.70 (see Example D).

7.21.

1-[[N-methyl-N-2-(methylamino)acetoxymethyl-3-methyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: colorless amorphous powder; FAB-MS: m/z 730 (M-HCl-I)$^+$. $^1$H-NMR (DMSO-d6): δ 1.20(3H, d, J=7.3 Hz), 1.50-1.86(3H, m), 2.32-2.55(6H, m), 3.12(3H, m), 3.82-4.20 (3H, m), 4.75-5.30(4H, m), 6.66-7.38(7H, m), 7.93(2H, br.d, J=8.3 Hz), 8.22(2H, br.d, J=8.3 Hz), 8.47(1H, br.s), 9.20(1H, m), 10.5(1H, m).

7.22.

1-[[N-ethoxycarbonyl-N-2-(methylamino)acetoxymethyl-phenyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: pale yellow solid. LC-MS: m/z 774 (M-HCl-Cl)$^+$.

7.23.

1-[[N-pivaloyl-N-2-(methylamino)acetoxymethyl-phenyl]carbamoyloxy]ethyl-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: pale yellow solid. LC-MS: m/z 786 (M-HCl-Cl)$^+$.

7.24.

1-[[N-(methylamino)acetoxyethyl-N-pivaloyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: white powder. LC-MS: m/z 724 (M-HCl-Cl)$^+$; Ratio of Retention Time in HPLC: 0.83 (see Example D).

7.25.

1-[[N-(methylamino)acetoxyethyl-N-ethoxycarbonyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: white powder; LC-MS: m/z 712 (M-HCl-Cl)$^+$; Ratio of Retention Time in HPLC: 0.69 (see Example D).

Example 8

1-[[N-ethyl-N-2-(ehylamino)ethyl]carbamoyloxy]ethyl-1-[(2R,3R)-2-(2,5-difluoro-phenyl)-2-hydroxy-3-[4-(4-cyanophenyl)thiazol-2-yl]butyl]-1H-[1,2,4]triazol-4-ium chloride hydrochloride a) Preparation of 1-[[N-ethyl-N-2-(t-butoxycarbonylehylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride To a solution of [N-ethyl-N-(tert-butoxycarbonyl ethylamino)ethyl]carbamic acid 1-chloro-ethyl ester (t) (500 mg, 1.55 mmol) in acetonitrile (1 ml) was added the azole compound of Example 5a) (438 mg, 1 mmol) and catalytic amount of sodium iodide at 60° C. After stirring overnight, the solvent was removed and extracted with ethyl acetate. The organic phase was washed with water and brine. The solvent was removed in vacuo. The residue was purified by column chromatography (ethyl acetate to 10% methanel-dichloromethane) to afford 1-[[N-ethyl-N-2-(t-butoxy carbonylehylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride (α) (654 mg, 0.860 mmol, 86%) as light brown amorphous.

b) Preparation of 1-[[N-ethyl-N-2-(ehylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride To a solution of 1-[[N-ethyl-N-2-(t-butoxycarbonylehylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride (618 mg, 0.813 mmol) in ethyl acetate (4 ml) was added 4N hydrogen chloride ethyl acetate solution (4 ml) at room temperature. After stirring for 1 hour, the solvent was removed in vacuo and the precipitate was washed with ethyl acetate. The precipitate was dried up to afford 1-[[N-ethyl-N-2-(ehylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride (505 mg, 0.725 mmol, 89%) as light brown amorphous. FAB-MS: 624 (M-HCl-Cl)$^+$; Physical form: light blown amorphous; $^1$H-NMR (DMSO): δ 0.90~1.30 (9H, m), 1.68~1.89 (3H, m), 2.71~3.75 (8H, m), 4.03~4.20 (1H, m), 4.66~4.87 (1H, m), 4.93~5.13 (1H, m), 6.65~6.98 (2H, m), 7.07~7.43 (3H, m), 7.93 (2H, d, J=7.92 Hz), 8.20 (2H, d, J=8.25 Hz), 8.48 (1H, s), 9.15~9.49 (2H, m), 10.48~10.68 (1H, m).

The following compounds in Examples 8.1-8.5. were obtained according to a manner analogous to those of Example 8.

8.1.
1-[[N-methyl-N-2(methylamino)ethyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 596 (M-HCl-Cl)$^+$; Ratio of Retention Time in HPLC: 0.81 (see Example D). $^1$H-NMR (DMSO): δ 1.10~1.28 (3H, m), 1.68~1.87 (3H, m), 2.76~2.92 (3H, m), 3.00 (2H, brs), 3.33~3.79 (2H, m), 4.02~4.20 (1H, m), 4.66~4.84 (1H, m), 4.98~5.10 (1H, m), 6.59~7.42 (7H, m), 7.93 (2H, d, J=8.25 Hz), 8.22 (2H, d, J=8.58 Hz), 8.48 (1H, s), 9.05~9.41 (3H, m), 10.46~10.64 (1H, m).

8.2.
1-[[N-methyl-N-3-(mehylamino)propyl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 610 (M-HCl-Cl)$^+$. $^1$H-NMR (DMSO): δ 1.12~1.29 (4H, m), 1.70~2.00 (6H, m), 2.68~2.95 (6H, m), 3.15~3.47 (1H, m), 4.07~4.25 (1H, m), 4.91 (2H, dd, J=14.18 Hz), 5.05 (1H, d, J=14.19 Hz), 6.63~6.79 (1H, m), 7.00~7.42 (3H, m), 7.73 (1H, brs), 7.95 (2H, d, J=8.25 Hz), 8.23 (2H, d, J=8.25 Hz), 8.48 (1H, s), 9.18~9.53 (3H, m), 10.45~10.68 (1H, m).

8.3.
1-[[3(S)-amino-pyrrolidin-1-yl]carbonyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydro-chloride. Physical form: colorless amorphous powder; FAB-MS: m/z 594 (M-HCl-Cl)$^+$; Ratio of Retention Time in HPLC: 0.81 (see Example D). $^1$H-NMR(DMSO-d$_6$): δ 1.19(3H, d, J=7.3 Hz), 1.75(3H, br.d, J=5.9 Hz), 1.97-2.22 (2H, m), 3.26-3.65(4H, m), 3.75(1H, m), 4.12(1H, m), 4.72-5.08(2H, m), 6.72(1H, m), 7.05-7.38(3H, m), 7.93(2H, d, J=8.3 Hz), 8.21 (2H, d, J=8.3 Hz), 8.46(1H, br.s), 8.60(3H, m), 9.21 (1H, m), 10.5(1H, m).

8.4.
1-[[2(S)-aminomethyl-pyrrolidin-1-yl]carbonyloxy]ethyl-1-[(2R,3R)-2-(2,5-difluoro-phenyl)-2-hydroxy-3-[4-(4-cyanophenyl)thiazol-2-yl]butyl]-1H-[1,2,4]triazol-4-ium chloride hydrochloride. Physical form: colorless amorphous powder; FAB-MS: m/z 608 (M-HCl-Cl)$^+$; Ratio of Retention Time in HPLC: 0.79 (see Example D). $^1$H-NMR(DMSO-d$_6$): δ 1.19(3H, m), 1.50-2.00(7H, m), 3.02-3.53(5H, m), 4.15 (1H, m), 4.74-5.07(2H, m), 6.72(1H, m), 7.05-7.38(3H, m), 7.93(2H, d, J=8.2 Hz), 8.21 (2H, d, J=8.2 Hz), 8.46(1H, br.s), 9.21 (1H, br.s), 10.4(1H, br.s).

8.5.
1-[[N-methyl-N-2-(methylamino)-1,2-trans-cyclohexan-1-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium iodide hydrochloride. Physical form: colorless amorphous powder; FAB-MS: m/z 650 (M-HCl-I)$^+$; Ratio of Retention Time in HPLC: 0.85 (see Example D). $^1$H-NMR(DMSO-d$_6$): δ 1.20(3H, d, J=7.3 Hz), 1.30-2.18(11H, m), 2.37-2.80(6H, m), 3.26(1H, m), 3.88(1H, m), 4.12(1H, m), 4.71-5.08(2H, m), 6.72(1H, m), 7.05-7.39 (3H, m), 7.93(2H, br.d), 8.21 (2H, d, J=8.6 Hz), 8.47(1H, br.s), 9.20(1H, m), 10.5(1H, m).

Example A

Manufacture of Dry Ampoules for Intramuscular Administration

A lyophilizate of 0.5 g of 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride is prepared in the usual manner and filled into an ampoule. Prior to the administration the lyophilizate is treated with 2.5 ml of a 2% aqueous lidocaine hydrochloride solution.

Example B

Hard gelatin capsules each containing the following ingredients were manufactured in the conventional manner per se:

| | |
|---|---|
| a) (1-[[N-methyl-N-3-[(methylamino)acetoxymethyl]pyridin-2-yl]carbamoyloxy]ethyl-1[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride | 100 mg |
| b) Lactose | 56 mg |
| c) Crystalline Cellulose | 30 mg |
| d) Silicic acid, Light Anhydrous | 10 mg |
| e) Talc | 3 mg |
| f) Magnesium stearate | 1 mg |
| Total | 200 mg |

Example C

Tablets each containing the following ingredients were manufactured in the conventional manner per se:

| | |
|---|---|
| a) 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium chloride hydrochloride | 100 mg |
| b) Lactose | 60 mg |
| c) Corn starch | 20 mg |
| d) Sodium Starch Glycolate | 10 mg |
| e) Polyvinylpyrrolidone | 6 mg |
| f) Talc | 3 mg |
| g) Magnesium stearate | 1 mg |
| Total | 200 mg |

Example D

HPLC Condition and Ratio of Retention Time of the compound of the general formula (I) HPLC Condition
1. Analytical Column: YMC-Pack ODS-AM (AM-313) 5 mm, 120A
   250×6.0 mml·D. (No. 062505696(W))
   with precolumn:YMC Guardpack ODS-AM,
   5 mm, 120A
   10×5.0 mml·D. (No. 4099(W))
2. Eluent: MeOH/CH$_3$CN/H$_2$O/AcOH=65:10:25:0.1 (v/v) containing
   1 g/L Sodium 1-Nonanesulfonate: mobile phase A
   or 1 g/L Sodium 1-Heptanesulfonate: mobile phase B
   or 1 g/L Sodium 1-Pentanesulfonate: mobile phase C
   or 1 g/L Sodium 1-Hexanesulfonate: mobile phase D
3. Flow Rate: 1.1 ml/min
4. Detection: Fluorescence Wavelength: Excitation: 280 nm Emission: 350 nm
5. Injection volume: 7 μl Instruments
1. Pump A: LC-10AS (Shimadzu) Pump B: LC-6A (Shimadzu)
2. Detector: FP-920 (JASCO)
3. Injector: SCL-10A/SIL-10A (Shimadzu) Run time: 18-30 min
4. Switching valve: PT-8000 (TOSOH)
5. Integrator: HPLC Chemstation Ratio of Retention Time of the Compound of the General Formula (I)

Ratio of Retention Time:

Retention time of compound of general formula (I)/ Retention time of standard compound of Example 5a)

Standard Compound of Example 5a):
(2R,3R)-3-[4-(4-cyanophenyl)thiazol-2-yl]-2-(2,5-difluorophenyl)-1-(1H-1,2,4-triazol-1-yl)-butan-2ol.

Retention Time of Standard compound of Example 5a):
   113.2 min for mobile phase A
   12.6 min for mobile phase B
   14.1 min for mobile phase C
   13.0 min for mobile phase D

TABLE
HPLC results

| Example No. | mobile phase | Ratio of retention time |
|---|---|---|
| 5 | A | 1.79 |
| 7 | B | 0.77 |
| 5.1. | B | 1.10 |
| 5.2. | B | 0.82 |
| 5.3. | B | 0.77 |
| 5.4. | A | 1.36 |
| 5.5. | A | 0.78 |
| 5.6. | B | 0.83 |
| 5.7. | B | 1.79 |
| 7.1. | B | 0.78 |
| 7.2. | B | 0.75 |
| 7.3. | B | 0.94 |
| 7.4. | B | 0.83 |
| 7.5. | B | 0.79 |
| 7.6. | B | 0.80 |
| 7.7. | D | 0.70 |
| 7.8. | D | 0.70 |
| 7.9. | B | 0.76 |
| 7.10. | B | 0.60 |
| 7.11. | B | 0.83 |
| 7.12. | A | 0.87 |
| 7.13. | B | 0.77 |
| 7.14. | C | 0.50 |
| 7.15. | B | 0.88 |
| 7.16. | B | 0.82 |
| 7.17. | A | 1.09 |
| 7.18. | B | 0.83 |
| 7.19. | B | 0.91 |
| 7.20. | B | 0.70 |
| 7.24. | B | 0.83 |
| 7.25. | B | 0.69 |
| 8.1. | B | 0.81 |
| 8.3. | B | 0.81 |
| 8.4. | B | 0.79 |
| 8.5. | B | 0.85 |

What is claimed is:

1. A triazole compound consisting of an anion selected from pharmaceutically acceptable anions and a cation represented by the formula

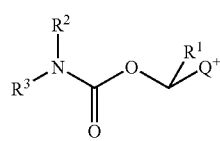

wherein
Q is a 1,2,4-triazole derivative selected from the group consisting of (2R, 3R)-3-[4-(4-cyanophenyl)thiazol-2-yl]-2-(2,4-difluorophenyl)-1-(1H-1,2,4-triazol-1-yl)butan-2-ol, (2R, 3R)-3-[4-(4-cyanophenyl)thiazol-2-yl[-1-(1H-1,2,4-triazol-1-yl)-2-(2,4,5-trifluorophenyl)-butan-2-ol and (2R, 3R)-3-[4-(4-cyanophenyl)thiazol-2-yl]-2-(3-fluorophenyl)-1-(1H-1,2,4-triazole-1-yl)-butan-2-ol, which triazole derivative is linked to the remainder of the said cation by a nitrogen in the triazole;
$R^1$ is hydrogen or alkyl;
$R^2$ is hydrogen, alkyl, alkylcarbonyloxyalkyl, alkoxycarbonyl, alkylcarbonyl, mono- or dialkylaminoalkylcarbonyloxyalkyl;
$R^3$ is pyridin-2-yl or substituted pyridin-2-yl, wherein $R^3$ is substituted pyridin-2-yl, said cation is represented by the formula

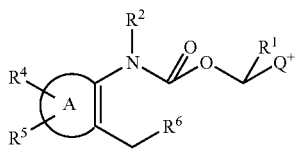

wherein

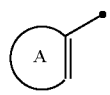

is pyridin-2-yl;
$R^4$ and $R^5$ are independently selected from the group consisting of hydrogen, halogen, alkyl, alkoxy, alkylthio, alkylsulfinyl, alkylsulfonyl, carboxy, alkyloxycarbonyl, cyano, trifluoromethyl, trifluoromethoxy, nitro, aminosulfonyl and sulfo; and
$R^6$ is selected from the group consisting of hydroxy, alkoxycarbonylalkylamino, alkoxycarbonylamino, amino, alkylamino, alkylcarbonyloxy, alkoxycarbonylalkylaminoalkylcarbonyloxy alkoxycarbonylaminoalkylcarbonyloxy, alkylaminoalkylcarbonyloxy, aminoalkylcarbonyloxy, alkylcarbonylamino, alkylcarbonylalkylamino, acyloxy, acylamino, and acylalkylamino, wherein said acyl is a hydrolizable radical; or a pharmaceutically acceptable salt thereof.

2. The compound of claim 1 wherein $R^4$ and $R^5$ are independently selected from the group consisting of hydrogen, halogen and alkoxy.

3. The compound of claim 2 wherein $R^4$ and $R^5$ are hydrogen.

4. The compound of claim 3 wherein $R^6$ is alkylaminoalkylcarbonyloxy.

5. The compound of claim 4 wherein $R^1$ is hydrogen or alkyl.

6. The compound of claim 5 wherein $R^2$ is alkyl.

7. The compound of claim 6, wherein Q is (2R, 3R)-3-[4-(4-cyanophenyl)thiazol-2-yl]-2-(2,4-difluorophenyl)-1-(1H-1,2,4-triazol-1-yl)butan-2-ol.

8. The compound of claim 1, wherein Q is (2R, 3R)-3-[4-(4-cyanophenyl)thiazol-2-yl]-2-(2,4-difluorophenyl)-1-(1H-1,2,4-triazol-1-yl)butan-2-ol, $R^1$ is hydrogen or alkyl, $R^2$ is alkyl, $R^4$ and $R^5$ are hydrogen, $R^6$ is alkylaminoalkylcarbonyloxy and said pharmaceutically acceptable anion is an anion of a pharmaceutically acceptable acid.

9. The compound of claim 1, wherein said cation is (2R, 3R)-1-[[N-methyl-N-3-[(methylamino)acetoxymethyl]pyridin-2-yl]carbamoyloxy]ethyl-1-2-(2,4-difluorophenyl)-2-hydroxy-3-[4-(4-cyanophenyl)thiazol-2-yl]butyl]-1H-[1,2,4]triazol-4-ium.

10. The compound of claim 1, wherein said compound is 1-[[N-methyl-N-3-[(methylamino)acetoxymethyl]pyridin-2-yl]carbamoyloxy]ethyl-1-[(2R,3R)-2-(2,4-difluorophenyl)-2-hydroxy-3-[4-(4-cyanophenyl)thiazol-2-yl ]butyl]-1H-[1,2,4]triazol-4-ium chloride or a pharmaceutically acceptable salt thereof.

11. The compound of claim 1, wherein said cation is 1-[[N-methyl-N-3-[(methylamino)acetoxymethyl]pyridin-2-yl]carbamoyloxy]ethyl-1[(2R,3R)-2-(2,4,5-trifluorophenyl)-2-hydroxy-3-[4-(4-cyanophenyl)thiazol-2-yl]butyl]-1H-[1,2,4]triazol-4-ium.

12. The compound of claim 1, wherein said compound is 1-[[N-methyl-N-3-[(methylamino)acetoxymethyl]pyridin-2]carbamoyloxy]ethyl-1-[(2R,3R)-2-(2,4,5-trifluorophenyl)-2-hydroxy-3-[4-(4-cyanophenyl)thiazol-2-yl]butyl]-1H-[1,2,4]triazol-4-ium chloride or a pharmaceutically acceptable salt thereof.

13. The compound of claim 1 wherein said cation is 1-[[N-methyl-N-3-[(methylamino)acetoxymethyl]pyridin-2-yl]carbamoyloxy]ethyl-1-[(2R,3R)-2-(3-fluorophenyl)-2-hydroxy-3-[4-(4-cyanophenyl)thiazol-2-yl]butyl]-1H-[1,2,4]triazol-4-ium.

14. The compound of claim 1, wherein said compound is 1-[[N-methyl-N-3-[(methylamino)acetoxymethyl]pyridin-2-yl]carbamoyloxy]ethyl-1-[(2R,3R)-2-(3-fluorophenyl)-2-hydroxy-3-[4-(4-cyanophenyl)thiazol-2-yl]butyl]-1H-[1,2,4]triazol-4-ium chloride or a pharmaceutically acceptable salt thereof.

15. A triazole compound consisting of an anion selected from pharmaceutically acceptable anions and a cation represented by the formula

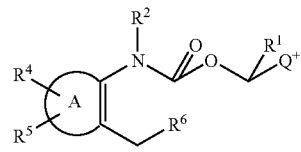

wherein

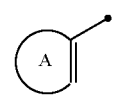

is pyridin-2-yl;
Q is a (2R,3R)-3-[4-(4-cyanophenyl)thiazol-2-yl)]-2-(2,5-difluorophenyl)-1-(1H-2,4-triazol-1-yl)-butan-2-ol moiety which is linked to the remainder of the cation by a nitrogen in the triazole;
$R^1$ is hydrogen or alkyl;
$R^2$ is hydrogen, alkyl, alkylcarbonyloxyalkyl, alkoxycarbonyl, alkylcarbonyl, mono- or dialkylaminoalkylcarbonyloxyalkyl;
$R^4$ and $R^5$ are independently selected from the group consisting of hydrogen, halogen, alkyl, alkoxy, alkylthio, alkylsulfinyl, alkylsulfonyl, carboxy, alkyloxycarbonyl, cyano, trifluoromethyl, trifluoromethoxy, nitro, aminosulfonyl, alkylaminocarboyloxyalkyl, sulfo, alkylcarbonyloxyalkyl and aminoalkylcarbonyloxyalkyl;

$R^6$ is alkylaminoalkylcarbonyloxy, or aminoalkylcarbonyloxy;

or a pharmaceutically acceptable salt thereof.

16. The triazole compound of claim 15 wherein $R^4$ and $R^5$ are independently selected from the group consisting of hydrogen, halogen and alkoxy.

17. The triazole compound of claim 16 wherein $R^4$ and $R^5$ are hydrogen.

18. The triazole compound of claim 17 wherein $R^2$ is alkyl.

19. The triazole compound of claim 15 wherein said cation is 1-[[N-methyl-N-3-[(methylamino)acetoxymethyl]pyridin-2-yl]carbamoyloxy]ethyl-1-[(2R,3R)-2-(2,5-difluorophenyl)-2-hydroxy-3-[4-(4-cyanophenyl)thiazol-2-yl]butyl]-1H-[1,2,4]triazol-4-ium.

20. The triazole compound of claim 15 wherein said cation is 1-[[N-methyl-N-3-[(methylamino)acetoxymethyl]pyridin-2-yl]carbamoyloxy]ethyl-1-[(2R,3R)-2-(2,5-difluorophenyl-2-hydroxy-3-[4-(4-cyanophenyl)thiazol-2-yl]butyl]-1H-[1,2,4]triazol-4-ium and said anion is an anion of a pharmaceutically acceptable inorganic acid.

21. The triazole compound of claims 20 wherein said anion is a chloride, bromide or sulfate.

\* \* \* \* \*

UNITED STATES PATENT AND TRADEMARK OFFICE
CERTIFICATE OF CORRECTION

PATENT NO. : 7,459,561 B2
APPLICATION NO. : 11/504299
DATED : December 2, 2008
INVENTOR(S) : Hiroshi Fukuda et al.

Page 1 of 1

It is certified that error appears in the above-identified patent and that said Letters Patent is hereby corrected as shown below:

In The Claims

Col. 54, line 58, "-(1H-2,4-triazol-1-yl)-" should be replaced with "-(1H-1,2,4-triazol-1-yl)-."

Signed and Sealed this
Nineteenth Day of July, 2016

Michelle K. Lee
*Director of the United States Patent and Trademark Office*